US008314127B2

(12) United States Patent
Austin et al.

(10) Patent No.: US 8,314,127 B2
(45) Date of Patent: *Nov. 20, 2012

(54) PIPERIDINE DERIVATIVES

(75) Inventors: Talbir Austin, Leicestershire (GB);
David O'Sullivan, Leicestershire (GB);
Matthew Perry, Leicestershire (GB);
Brian Springthorpe, Leicestershire (GB)

(73) Assignee: Astrazeneca AB, Sodertalje (SE)

( * ) Notice: Subject to any disclaimer, the term of this patent is extended or adjusted under 35 U.S.C. 154(b) by 1152 days.

This patent is subject to a terminal disclaimer.

(21) Appl. No.: 11/996,133

(22) PCT Filed: Jul. 19, 2006

(86) PCT No.: PCT/SE2006/000893
§ 371 (c)(1),
(2), (4) Date: Jan. 18, 2008

(87) PCT Pub. No.: WO2007/011293
PCT Pub. Date: Jan. 25, 2007

(65) Prior Publication Data
US 2008/0207688 A1 Aug. 28, 2008

(30) Foreign Application Priority Data

Jul. 21, 2005 (SE) .................................. 0501719
Apr. 13, 2006 (SE) .................................. 0600838

(51) Int. Cl.
*A61K 31/4545* (2006.01)
*C07D 211/46* (2006.01)
(52) U.S. Cl. ......... 514/316; 546/187; 546/188; 546/190
(58) Field of Classification Search ............... 514/316; 546/187, 188, 190
See application file for complete search history.

(56) References Cited

U.S. PATENT DOCUMENTS

| 4,505,915 | A | 3/1985 | Hannah |
| 4,588,722 | A | 5/1986 | Janssens et al. |
| 4,695,575 | A | 9/1987 | Janssens et al. |
| 5,883,096 | A | 3/1999 | Lowe et al. |
| 5,889,006 | A | 3/1999 | Lowe et al. |
| 5,952,349 | A | 9/1999 | Asberom et al. |
| 5,977,138 | A | 11/1999 | Wang et al. |
| 6,066,636 | A | 5/2000 | Kozlowski et al. |
| 6,294,554 | B1 | 9/2001 | Clader et al. |
| 6,387,930 | B1 | 5/2002 | Baroudy et al. |
| 6,440,440 | B1 | 8/2002 | Meerpoel et al. |
| 6,525,070 | B2 | 2/2003 | Rigby et al. |
| 6,759,411 | B2 | 7/2004 | Ko et al. |
| 6,903,115 | B2 | 6/2005 | Rigby et al. |
| 7,179,922 | B2 | 2/2007 | Lawrence et al. |
| 7,186,718 | B2 | 3/2007 | Gustafsson et al. |
| 7,238,691 | B2 | 7/2007 | Sanganee et al. |
| 7,238,811 | B2 | 7/2007 | Lawrence et al. |
| 7,265,227 | B2 | 9/2007 | Evans et al. |
| 7,307,090 | B2 | 12/2007 | Evans et al. |
| 7,495,013 | B2 | 2/2009 | Caffrey et al. |
| 7,517,989 | B2 | 4/2009 | Luckhurst et al. |
| 2005/0176708 | A1 | 8/2005 | Luckhurst et al. |
| 2005/0182094 | A1 | 8/2005 | Sanganee et al. |
| 2006/0040984 | A1 | 2/2006 | Luckhurst et al. |
| 2006/0264463 | A1 | 11/2006 | Luckhurst et al. |
| 2006/0281726 | A1 | 12/2006 | Luckhurst et al. |
| 2007/0032523 | A1 | 2/2007 | Caffrey et al. |
| 2007/0179297 | A1 | 8/2007 | Lawrence et al. |

FOREIGN PATENT DOCUMENTS

| EP | 0 099 139 | 1/1984 |
| EP | 0 121 972 | 10/1984 |
| EP | 0 145 037 | 6/1985 |
| EP | 0 151 824 | 8/1985 |
| EP | 0 151 826 | 8/1985 |
| EP | 1 076 055 | 2/2001 |
| EP | 1 362 857 | 11/2003 |
| EP | 1 389 616 | 2/2004 |
| GB | 1250719 | 10/1971 |
| GB | 2 373 186 | 9/2002 |
| WO | WO 93/10091 | 5/1993 |
| WO | WO 95/08535 | 3/1995 |
| WO | WO 96/26196 | 8/1996 |
| WO | WO 96/34857 | 11/1996 |
| WO | WO 96/41631 | 12/1996 |
| WO | WO 97/24324 | 7/1997 |
| WO | WO 98/01425 | 1/1998 |
| WO | WO 98/05291 | 2/1998 |
| WO | WO 98/05292 | 2/1998 |
| WO | WO 98/06697 | 2/1998 |
| WO | WO 98/11128 | 3/1998 |
| WO | WO 99/04794 | 2/1999 |
| WO | WO 99/37304 | 7/1999 |
| WO | WO 99/38514 | 8/1999 |
| WO | WO 99/51578 | 10/1999 |
| WO | WO 99/55324 | 11/1999 |

(Continued)

OTHER PUBLICATIONS

Seddon "Pseudopolymorph . . . " Crystal growth & design p. 1087 (2004) (two pares form internet).*
Braga et al. :Making crystals . . . J. royal Soc. chem. Chem. Commun. p. 3635-3645 (2005).*
Austin et al. "Preparation of novel piperidine . . . " CA146:184370 (2007).*
Caffreu et a;/ "A preparation of piperinylmethyl . . . " CA141:332063 (2004).*
Hoffman et al., "The Preparation of 2-Hydrazinyl Esters in High Optical Purity from 2-Sulfonyloxy Esters", *Tetrahedron Letters* 31(21):2953-2956 (1990).
Allain et al., (2005) STN International, HCAPLUS Database, Columbus, OH, Accession No. 1992:187881, Reg. No. 46817-91-8, citing "Antidepressants and cognition: comparative effects of moclobemide, viloxazine and maprotiline", *Psychopharmacology* 106 (Suppl.), (1992).

(Continued)

*Primary Examiner* — Celia Chang
(74) *Attorney, Agent, or Firm* — Astrazeneca AB

(57) ABSTRACT

The present invention provides a compound of a formula (I): wherein the variables are defined herein; to a process for preparing such a compound; and to the use of such a compound in the treatment of a chemokine (such as CCR3) mediated disease state.

3 Claims, 2 Drawing Sheets

FOREIGN PATENT DOCUMENTS

Figure 1:
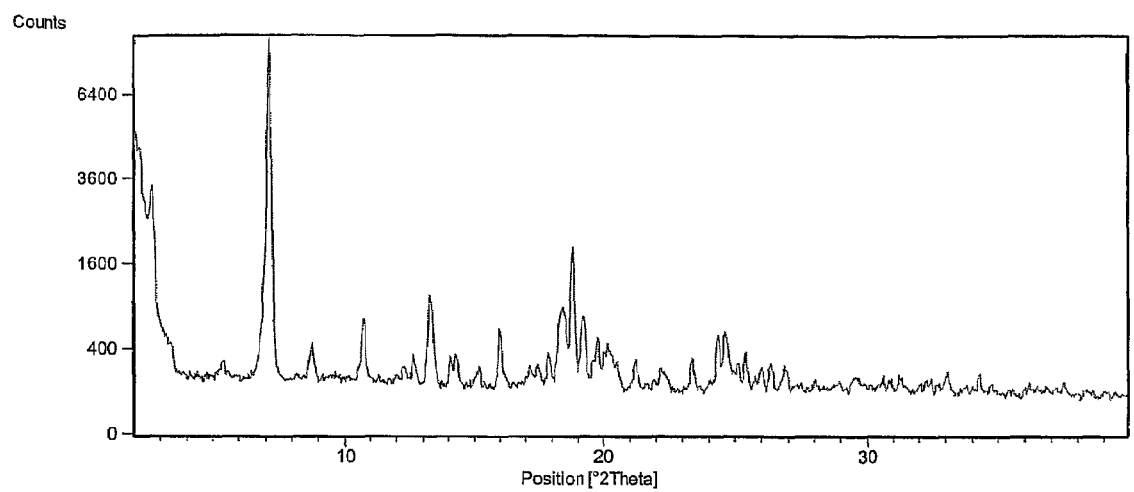

| | | |
|---|---|---|
| WO | WO 00/00488 | 1/2000 |
| WO | WO 00/12478 | 3/2000 |
| WO | WO 00/32590 | 6/2000 |
| WO | WO 00/35877 | 6/2000 |
| WO | WO 00/66559 | 11/2000 |
| WO | WO 01/02381 | 1/2001 |
| WO | WO 01/07436 | 2/2001 |
| WO | WO 01/29066 | 4/2001 |
| WO | WO 01/77101 | 10/2001 |
| WO | WO 01/92227 | 12/2001 |
| WO | WO 02/18335 | 3/2002 |
| WO | WO 02/20484 | 3/2002 |
| WO | WO 02/066460 | 8/2002 |
| WO | WO 02/072570 | 9/2002 |
| WO | WO 02/079190 | 10/2002 |
| WO | WO 02/079194 | 10/2002 |
| WO | WO 02/081449 | 10/2002 |
| WO | WO 03/004487 | 1/2003 |
| WO | WO 03/018576 | 3/2003 |
| WO | WO 03/020716 | 3/2003 |
| WO | WO 03/022277 | 3/2003 |
| WO | WO 03/024962 | 3/2003 |
| WO | WO 03/078395 | 9/2003 |
| WO | WO 03/078421 | 9/2003 |
| WO | WO 2004/029041 A1 | 4/2004 |
| WO | WO 2004/085423 | 10/2004 |
| WO | WO 2004/087659 A1 | 10/2004 |
| WO | WO 2004/099144 | 11/2004 |
| WO | WO 2004/113323 | 12/2004 |
| WO | WO 2005/097775 | 10/2005 |
| WO | WO 2006/126947 | 11/2006 |
| WO | WO 2006/126948 | 11/2006 |
| WO | WO 2007/011293 | 1/2007 |

OTHER PUBLICATIONS

Cohen et al., *Am. J. Clin. Pathol.* 105:589 (1996).
Harada et al., "Novel *N*-[1-(1-Substituted 4-Piperidinylmethyl)-4-piperidinyl]benzamides as Potent Colonic Prokinetic Agents", *Bioorganic & Medicinal Chemistry Letters* 12:967-970 (2002).
Hermans et al., "4-Substituted Piperidines. II. Reaction of 1-Benzyl-4-cyano-4-*t*-aminopiperidines with Organometallic Compounds", *J. Med. Chem.* 8(6):851-855 (1965) at p. 852 ("compound 12" in Table I).
Hodgson et al., "Chemokines and Drug Discovery", *Drug New Perspect* 17(5):335-338 (2004).
Patani and LaVoie, "Bioisosterism: A Rational Approach in Drug Design", *Chem. Rev.* 96:3147-3176 (1996).
STN International, File CAPLUS, CAPLUS accession No. 1988:630911, Document No. 109:230911, Lehmann, Jochen et al: "Lactones. XVIII. Synthesis of lactone-bridged 1,1-diarylpropanamines"; & *Arch. Pharm.* (Weinheim, Ger.) (1988), 321(7), 443-445.
Braga et al., "Making crystals from crystals: a green route to crystal engineering and polymorphism", *J. Roy. Soc. Chem. Chem. Commun.* 3635-3645 (2005).
Brown et al., "Novel CCR1 antagonists with improved metabolic stability", *Bioorg. Med. Chem. Lett.*14:2175-2179 (2004).
Lawrence et al., "Synthesis of substituted bipiperidines and their use as H1 antagonists", CAPLUS 135:318419 (2001) (not necessary to cite; previously cited as WO 01/77101).
Luckhurst et al., "Preparation of 1-(piperidin-3-ylmethyl)piperidines and 2-(piperidin-1-ylmethyl)morpholines as modulators of chemokine receptor activity", CAPLUS 139:276907 (2003) (not necessary to cite; previously cited as WO 03/078395).
Machii et al., "Preparation of 5-cyanopyrimidine derivatives as anti-inflammatory agents", CAPLUS 139:307788 (2003).
Mattson et al., "Preparation of [(oxopyrrolidinylmethyl)piperidinyl]pyrimidines as nootropics and memory enhancers", CAPLUS 116:151786 (1992).
Seddon, "*Pseudo*polymorph: A Polemic", *Crystal Growth & Design* 4:1087 (2004) (two pages from Internet).
Thoma et al., "Orally Bioavailable Competitive CCR5 Antagonists", *J. Med. Chem.* 47:1939-1955 (2004).
Ting et al., "The synthesis of substituted bipiperidine amide compounds as CCR3 ligands: Antagonists versus agonists", *Bioorg. Med. Chem. Lett.*15:3020-3023 (2005).
West, "Solid Solutions", *Solid state chemistry and its applications*, pp. 358 & 365 (1988).
Xie et al., "Identification of novel series of human CCR1 antagonists", *Bioorg. Med. Chem. Lett.* 18:2215-2221 (2008).
Baroudy et al., "Preparation of piperidine derivatives as CCR5 antagonists", CAPLUS 133:350146 (2000).
Lowe et al., "Preparation of piperazine and piperidine derivatives as muscarinic antagonists" CAPLUS 128:180426 (1998).

\* cited by examiner

PIPERIDINE DERIVATIVES

CROSS-REFERENCE TO RELATED APPLICATIONS

This application is a national phase application under 35 U.S.C. §371 of PCT International Application No. PCT/SE2006/000893, filed Jul. 19, 2006, which claims the benefit of Swedish Application Serial No. 0501719-9, filed Jul. 21, 2005 and Swedish Application Serial No. 0600838-7, filed Apr. 13, 2006. Each of these prior applications is incorporated herein by reference in its entirety.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO 2004/087659. (2S)-2-[4-[[4-(3,4-Dichloro-2-methyl-phenoxy)-1-piperidyl]methyl]-1-piperidyl]-3-phenylpropanoic acid and its dihydrochloride salt are disclosed in WO 2004/087659 (see examples 40 and 73). Compounds of present invention have higher potency at CCR3 than comparable compounds in WO 2004/087659 [which translates to a lower dose meaning less serious side-effects, for example at the Ikr channel (for example using the assay described in WO 2005/037052, or the electrophysiology method described in the paper: 'Optimisation and validation of a medium-throughput electrophysiology-based hERG assay using IonWorks™ HT' by M. H. Bridgland-Taylor, C. E. Pollard et al in Journal of Pharmacological and Toxicological Methods (2006; available on the internet Elsevier publications www-.sciencedirect.com, and in press))]. The higher potency of the compounds of the invention also translates to increased selectivity over the histamine type 1 (H1) receptor.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, for example rhinitis or urticaria. H1 antagonists are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin, eotaxin-2, eotaxin-3 and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

Figure 2:
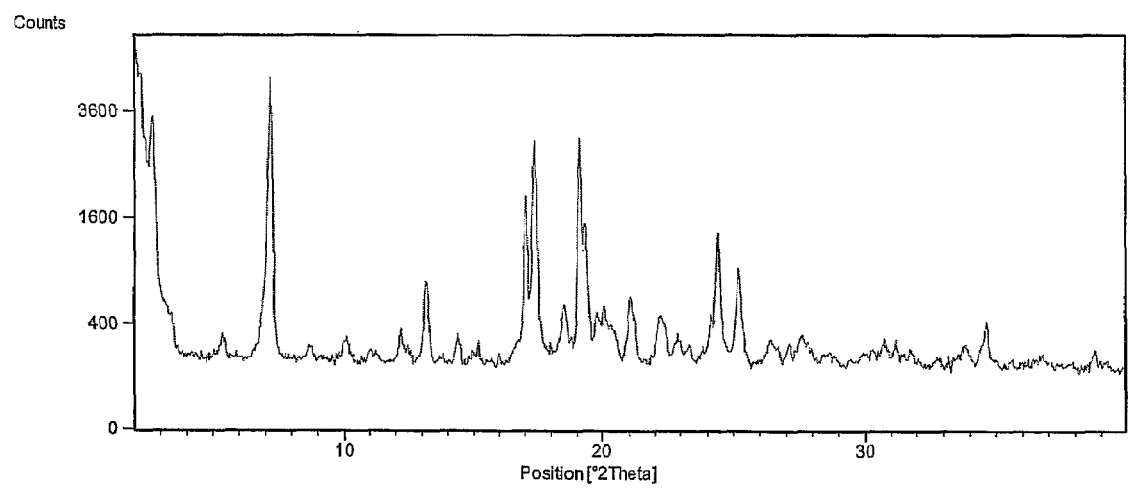
Figure 4:
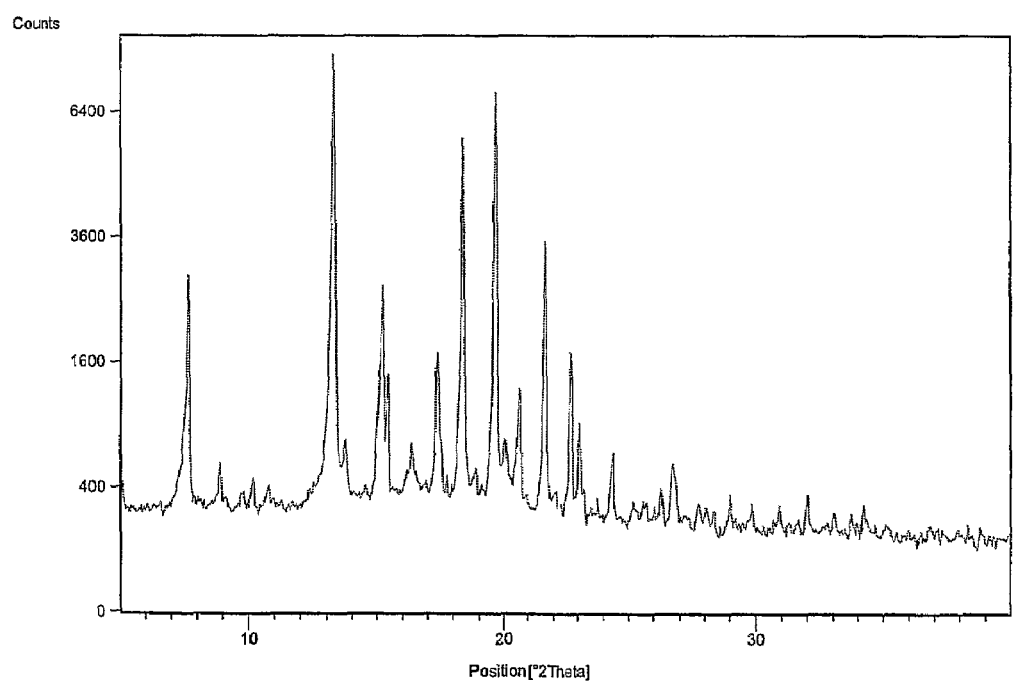

FIG. 1—XPRD of form I, example 28.
FIG. 2—XPRD of form II, example 29.
FIG. 2—XPRD of form A, example 32.
FIG. 4—XPRD of form B, example 34.

The present invention provides a compound of formula (I):

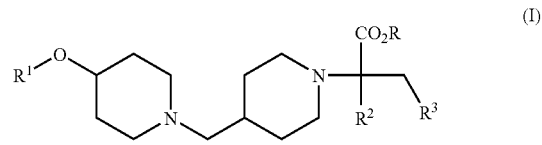

wherein:
$R^1$ is phenyl optionally substituted by halogen, cyano, $C_{1-4}$ alkyl or $C_{1-4}$ alkoxy;
$R^2$ is methyl or ethyl;
R is hydrogen, or $CO_2R$ is $(CO_2^-)_p R^{p+}$ wherein $R^{p+}$ is a univalent cation (for example an alkali metal cation) or two carboxylates may coordinate a divalent cation (for example an alkaline earth metal cation);
p is 1 or 2;
$R^3$ is phenyl optionally substituted with halogen, cyano, $C_{1-4}$ alkyl, $C_{1-4}$ alkoxy, $CF_3$ or $OCF_3$;
when $R^1$ is 2-methyl-3,4-dichlorophenyl and $R^3$ is 4-fluorophenyl, 4-cyanophenyl or 2-methoxyphenyl, then $R^2$ can also be hydrogen;
or an N-oxide thereof; or a pharmaceutically acceptable salt thereof.

Compounds of formula (I) wherein $R^2$ is methyl are surprisingly more soluble (sometimes up to 10 times more soluble) in certain solvents (for example phosphate buffer at pH 7.4) than compounds of formula (I) wherein $R^2$ is hydrogen. The increased solubility is advantageous for a oral pharmaceutical as the active ingredient will be more readily available for absorption from the gastrointestinal tract.

Certain compounds of the present invention can exist in different isomeric forms (such as enantiomers, diastereomers, geometric isomers or tautomers). The present invention covers all such isomers and mixtures thereof in all proportions.

The compounds of the invention can be zwitterionic and all such zwitterions are within the invention.

Suitable pharmaceutically acceptable salts include acid addition salts such as a hydrochloride, dihydrochloride, hydrobromide, phosphate, sulfate, acetate, fumarate, maleate, malonate, succinate, tartrate, citrate, oxalate, methanesulfonate, benzenesulfonate or p-toluenesulfonic acid. $(CO_2^-)_p R^{p+}$ are salts of the invention.

An alkali metal cation is, for example sodium or potassium, and an alkaline earth metal cation is, for example, magnesium or calcium.

The univalent cation $R^{p+}$, wherein p is 1, can also be, for example, a protonated tertiary amine such as $(CH_2CH_2OH)_3NH^+$.

The compounds of the invention may exist as solvates (such as hydrates) and the present invention covers all such solvates. Examples of alternative solvates include compounds of the invention having ethanol or ethyl acetate included in the solid phase. Solvates can exist as, for example, a compound of the invention having solvate molecules within the crystal lattice, or, where solvent is within one or more channels within the crystal lattice (such as a channel hydrate), or a mixture of these two.

Halogen includes fluorine, chlorine, bromine and iodine. Halogen is, for example, fluorine or chlorine.

Alkyl is straight or branched chain and is, for example, methyl, ethyl, n-propyl, iso propyl or tert-butyl.

In one particular aspect the present invention provides a compound of formula (I) wherein: $R^1$ is phenyl optionally substituted by halogen, cyano, $C_{1-4}$ alkyl or $C_{1-4}$ alkoxy; $R^2$ is methyl; R is hydrogen, or $CO_2R$ is $(CO_2^-)_p R^{p+}$ wherein $R^{p+}$ is a univalent cation (for example an alkali metal cation) or two carboxylates may coordinate a divalent cation (for example an alkaline earth metal cation); p is 1 or 2; $R^3$ is phenyl optionally substituted with halogen, cyano, $C_{1-4}$ alkyl, $C_{1-4}$ alkoxy, $CF_3$ or $OCF_3$; when $R^1$ is 2-methyl-3,4-dichlorophenyl and $R^3$ is 4-fluorophenyl, 4-cyanophenyl or 2-methoxyphenyl, then $R^2$ can also be hydrogen; or an N-oxide thereof; or a pharmaceutically acceptable salt thereof.

In a farther aspect the present invention provides a compound of formula (I) wherein: $R^1$ is phenyl optionally substituted by halogen, cyano, $C_{1-4}$ alkyl or $C_{1-4}$ alkoxy; $R^2$ is methyl; R is hydrogen, or $CO_2R$ is $(CO_2^-)_p R^{p+}$ wherein $R^{p+}$ is a univalent cation (for example an alkali metal cation) or two carboxylates may coordinate a divalent cation (for example an alkaline earth metal cation); p is 1 or 2; $R^3$ is phenyl optionally substituted with halogen, cyano, $C_{1-4}$ alkyl, $C_{1-4}$ alkoxy, $CF_3$ or $OCF_3$; when $R^1$ is 2-methyl-3,4-dichlorophenyl and $R^3$ is 4-fluorophenyl, 4-cyanophenyl or 2-methoxyphenyl, then $R^2$ can also be hydrogen; or a pharmaceutically acceptable salt thereof.

In another aspect the present invention provides a compound of formula (I) wherein, $R^1$ is phenyl optionally substituted by halogen, cyano, $C_{1-4}$ alkyl or $C_{1-4}$ alkoxy; $R^2$ is methyl; R is hydrogen, or $CO_2R$ is $(CO_2^-)_p R^{p+}$ wherein $R^{p+}$ is a univalent cation (for example an alkali metal cation) or two carboxylates may coordinate a divalent cation (for example an alkaline earth metal cation); p is 1 or 2; $R^3$ is phenyl optionally substituted with halogen, cyano, $C_{1-4}$ alkyl, $C_{1-4}$ alkoxy, $CF_3$ or $OCF_3$; or a pharmaceutically acceptable salt thereof.

In a further aspect the present invention provides a compound wherein $R^1$ is phenyl optionally substituted (for example with two or three of the same or different) with fluorine, chlorine, cyano, $C_{1-4}$ alkyl (for example methyl) or $C_{1-4}$ alkoxy (for example methoxy).

In another aspect the present invention provides a compound wherein $R^1$ is phenyl optionally substituted (for example with two or three of the same or different) with fluorine, chlorine, cyano or $C_{1-4}$ alkyl (for example methyl).

In yet another aspect the present invention provides a compound wherein $R^1$ is phenyl substituted by two or three substituents independently selected from: fluorine, chlorine, cyano and methyl.

In a further aspect the present invention provides a compound wherein $R^1$ is phenyl substituted by two or three substituents independently selected from: chlorine and methyl. For example $R^1$ is 3,4-dichlorophenyl, 4-chloro-2-methylphenyl, 2,4-dichloro-3-methylphenyl or 3,4-dichloro-2-methylphenyl. $R^1$ can also be 4-fluoro-2-methylphenyl or 4-chloro-3-methylphenyl. For example $R^1$ is 3,4-dichloro-2-methylphenyl. For example $R^1$ is 4-chloro-2-methylphenyl.

In a still further aspect the present invention provides a compound of formula (I) wherein R is hydrogen.

In another aspect the present invention provides a compound of formula (I) wherein $CO_2R$ is $CO_2$—$R^+$, wherein $R^+$ is sodium or potassium.

In yet another aspect $R^2$ is methyl.

In a still further aspect the present invention provides a compound of formula (I) wherein $R^2$ is hydrogen and $R^3$ is 4-fluorophenyl, 4-cyanophenyl or 2-methoxyphenyl (for example $R^3$ is 4-fluorophenyl).

The invention further provides (2S)-2-(4-{[4-(4-chloro-2-methylphenoxy)piperidin-1-yl]methyl}piperidin-1-yl)-3-(4-fluorophenyl)-2-methylpropanoic acid or a pharmaceutically acceptable salt thereof (for example a sodium, potassium or $(CH_2CH_2OH)_3NH^+$ salt, or an acid addition salt, such as a hydrochloride, dihydrochloride, hydrobromide, phosphate, sulfate, acetate, fumarate, maleate, malonate, succinate, tartrate, citrate, oxalate, methanesulfonate, benzenesulfonate or p-toluenesulfonic acid).

In a still further aspect the present invention provides (2S)-2-(4-{[4-(4-chloro-2-methylphenoxy)piperidin-1-yl]methyl}piperidin-1-yl)-3-(4-fluorophenyl)-2-methylpropanoic acid.

In another aspect the present invention provides a polymorph of (2S)-2-(4-{[4-(4-chloro-2-methylphenoxy)piperidin-1-yl]methyl}piperidin-1-yl)-3-(4-fluorophenyl)-2-methylpropanoic acid hydrate (Form A) {water of varying stoichiometry, for example 1.5-2.5 equivalents} having an X-ray powder diffraction pattern containing specific peaks at: 5.3 (±0.1°), 10.6 (±0.1°), 12.3 (±0.1°), 12.9 (±0.1°), 13.9 (±0.1°), 15.5 (±0.1°), 15.9 (±0.1°), 16.9 (±0.1°), 19.6 (±0.1°), 20.0 (±0.1°), 20.4 (±0.1°), 21.1 (±0.1°), 21.5 (±0.1°), 24.0 (±0.1°), 24.8 (±0.1°), 25.1 (±0.1°), 25.8 (±0.1°), 29.4 (±0.1°) and 29.6 (±0.1°) 2θ.

In yet another aspect the present invention provides a polymorph of (2S)-2-(4-{[4-(4-chloro-2-methylphenoxy)piperidin-1-yl]methyl}piperidin-1-yl)-3-(4-fluorophenyl)-2-methylpropanoic acid ethanol solvate (Form B) having an X-ray powder diffraction pattern containing specific peaks at: 7.7 (±0.1°), 13.3 (±0.1°), 15.2 (±0.1°), 15.4 (±0.1°), 17.4 (±0.1°), 18.4 (±0.1°), 19.7 (±0.1°), 20.6 (±0.1°), 21.7 (±0.1°) and 22.7 (±0.1°) 2θ.

In another aspect the present invention provides a compound wherein $R^3$ is phenyl optionally substituted with halogen (such as fluoro), cyano or $C_{1-4}$ alkoxy (such as methoxy).

In yet another aspect the present invention provides a compound of formula (I) wherein $R^2$ is methyl and $R^3$ is fluorophenyl (for example 4-fluorophenyl).

In another aspect the present invention provides (S)-{4-[4-(3,4-dichloro-2-methyl-phenoxy)-piperidin-1-ylmethyl]-piperidin-1-yl}-3-(4-fluoro-phenyl)-propionic acid or a pharmaceutically acceptable salt thereof (for example a sodium, potassium or $(CH_2CH_2OH)_3NH^+$ salt, or an acid addition salt, such as a hydrochloride, dihydrochloride, hydrobromide, phosphate, sulfate, acetate, fumarate, maleate, malonate, succinate, tartrate, citrate, oxalate, methanesulfonate, benzenesulfonate or p-toluenesulfonic acid).

In yet another aspect the present invention provides (S)-{4-[4-(3,4-dichloro-2-methyl-phenoxy)-piperidin-1-ylmethyl]-piperidin-1-yl}-3-(4-fluoro-phenyl)-propionic acid.

In a further aspect the present invention provides a polymorph of (S)-{4-[4-(3,4-dichloro-2-methyl-phenoxy)-piperidin-1-ylmethyl]-piperidin-1-yl}-3-(4-fluoro-phenyl)-propionic acid (Form I) having an X-ray powder diffraction pattern containing specific peaks at: 2.2 (±0.1°), 2.7 (±0.1°), 7.1 (±0.1°), 10.7 (±0.1°), 13.3 (±0.1°) and 18.8 (±0.1°) 2 θ.

In a still further aspect the present invention provides a polymorph of (S)-{4-[4-(3,4-dichloro-2-methyl-phenoxy)-piperidin-1-ylmethyl]-piperidin-1-yl}-3-(4-fluoro-phenyl)-propionic acid (Form II) having an X-ray powder diffraction pattern containing specific peaks at: 2.2 (±0.1°), 2.67 (±0.1°), 7.2 (±0.1°), 13.2 (±0.1°), 17.0 (±0.1°), 17.4 (±0.1°), 19.1 (±0.1°), 19.4 (±0.1°), 21.1 (±0.1°), 24.4 (±0.1°) and 25.2 (±0.1°) 2θ.

In a further aspect the present invention provides a pharmaceutically acceptable salt of a compound of formula (I), having the (2S) absolute configuration, wherein $R^1$ is 2-methyl-3,4-dichlorophenyl, $R^2$ is hydrogen and $R^3$ is phenyl, provided it is not the dihydrochloride salt; such as a methanesulfonate or benzenesulfonate salt.

In another aspect the present invention provides a salt of (2S)-2-[4-[[4-(3,4-dichloro-2-methyl-phenoxy)-1-piperidyl]methyl]-1-piperidyl]-3-phenylpropanoic acid, but not the dihydrochloride salt, [for example an alkali metal salt (such as a sodium or potassium salt) or an acid addition salt (such as one of those listed above, for example a methanesulfonic acid or benzenesulfonic acid salt)]. In yet another aspect the present invention provides a sodium or potassium (for example a sodium salt) of (2S)-2-[4-[[4-(3,4-dichloro-2-methyl-phenoxy)-1-piperidyl]methyl]-1-piperidyl]-3-phenyl-propanoic acid.

In a further aspect the present invention provides one of the following individualised compounds of the invention:

(2S)-2-[4-[[4-(3,4-dichloro-2-methyl-phenoxy)-1-piperidyl]methyl]-1-piperidyl]-3-(4-fluorophenyl)-propanoic acid;

(2S)-2-[4-[[4-(3,4-dichloro-2-methyl-phenoxy)-1-piperidyl]methyl]-1-piperidyl]-3-(2-methoxyphenyl)-propanoic acid;

(2S)-3-(4-cyanophenyl)-2-[4-[[4-(3,4-dichloro-2-methyl-phenoxy)-1-piperidyl]methyl]-1-piperidyl]-propanoic acid;

(2S)-2-[4-[[4-(3,4-dichloro-2-ethyl-phenoxy)-1-piperidyl]methyl]-1-piperidyl]-3-phenylpropanoic acid;

(2S)-2-[4-[[4-(3,4-dichloro-2-ethyl-phenoxy)-1-piperidyl]methyl]-1-piperidyl]-3-(4-fluorophenyl)-propanoic acid;

(2S)-2-(4-{[4-(3-chloro-4-cyano-2-methylphenoxy)piperidin-1-yl]methyl}piperidin-1-yl)-3-phenylpropanoic acid;

(2S)-2-(4-{[4-(3-chloro-4-cyano-2-methylphenoxy)piperidin-1-yl]methyl}piperidin-1-yl)-3-(4-fluorophenyl)propanoic acid;

(2S)-2-[4-[[4-(2,4-dichloro-3-methyl-phenoxy)-1-piperidyl]methyl]-1-piperidyl]-3-(4-fluorophenyl)-propanoic acid;

(2S)-2-[4-[[4-(4-chloro-2-methyl-phenoxy)-1-piperidyl]methyl]-1-piperidyl]-3-(4-fluorophenyl)-propanoic acid;

(2S)-2-[4-[[4-(2,4-dichloro-phenoxy)-1-piperidyl]methyl]-1-piperidyl]-3-(4-fluorophenyl)-propanoic acid;

(S)-2-(4-{[4-(3,4-dichlorophenoxy)piperidin-1-yl]methyl}piperidin-1-yl)-3-(4-fluorophenyl)-2-methylpropanoic acid;

(S)-2-[4-[[4-(4-chloro-2-methyl-phenoxy)-1-piperidyl]methyl]-1-piperidyl]-3-(4-fluorophenyl)-2-methyl-propanoic acid;

(S)-2-[4-[[4-(3,4-dichloro-2-methyl-phenoxy)-1-piperidyl]methyl]-1-piperidyl]-3-(4-fluorophenyl)-2-methyl-propanoic acid;

Isomer 1 of 2-[4-[[4-(3,4-dichloro-2-methyl-phenoxy)-1-piperidyl]methyl]-1-piperidyl]-2-methyl-3-phenyl-propanoic acid;

Isomer 2 of 2-[4-[[4-(3,4-dichloro-2-methyl-phenoxy)-1-piperidyl]methyl]-1-piperidyl]-2-methyl-3-phenyl-propanoic acid;

2-(4-{[4-(3,4-dichloro-2-methylphenoxy)piperidin-1-yl]methyl}piperidin-1-yl)-2-methyl-3-phenylpropanoic acid;

Isomer 1 of 2-[4-[[4-(3,4-dichlorophenoxy)-1-piperidyl]methyl]-1-piperidyl]-2-methyl-3-phenyl-propanoic acid;

Isomer 2 of 2-[4-[[4-(3,4-dichlorophenoxy)-1-piperidyl]methyl]-1-piperidyl]-2-methyl-3-phenyl-propanoic acid;

(+)-2-[4-[[4-(3,4-dichloro-2-methyl-phenoxy)-1-piperidyl]methyl]-1-piperidyl]-2-methyl-3-phenyl-propanoic acid;

(2S)-2-[4-[[4-(3,4-dichloro-2-methyl-phenoxy)-1-piperidyl]methyl]-1-piperidyl]-3-phenylpropanoic acid sodium salt;

(2S)-2-[4-[[4-(3,4-dichloro-2-methyl-phenoxy)-1-piperidyl]methyl]-1-piperidyl]-3-(4-fluorophenyl)-propanoic acid sodium salt;

(2S)-2-[4-[[4-(3,4-dichloro-2-methyl-phenoxy)-1-piperidyl]methyl]-1-piperidyl]-3-(4-fluorophenyl)-propanoic acid potassium salt;

(2S)-2-[4-[[4-(3,4-dichloro-2-methyl-phenoxy)-1-piperidyl]methyl]-1-piperidyl]-3-phenylpropanoic acid methanesulfonic acid salt;

(2S)-2-[4-[[4-(3,4-dichloro-2-methyl-phenoxy)-1-piperidyl]methyl]-1-piperidyl]-3-phenylpropanoic acid benzenesulfonic acid salt;

(2S)-2-[4-[[4-(3,4-dichloro-2-methyl-phenoxy)-1-piperidyl]methyl]-1-piperidyl]-3-(4-fluorophenyl)-propanoic acid benzenesulfonic acid salt;

(2S)-2-[4-[[4-(3,4-dichloro-2-methyl-phenoxy)-1-piperidyl]methyl]-1-piperidyl]-3-(4-fluorophenyl)-propanoic acid hydrochloride;

2-Benzyl-2-(4-{[4-(3,4-dichlorophenoxy)piperidin-1-yl]methyl}piperidin-1-yl)butanoic acid;

(S)-2-{4-[4-(3,4-dichloro-2-methyl-phenoxy)-piperidin-1-ylmethyl]-piperidin-1-yl}-3-phenyl-propionic acid;

(S)-{4-[4-(3,4-dichloro-2-methyl-phenoxy)-piperidin-1-ylmethyl]-piperidin-1-yl}-3-(4-fluoro-phenyl)-propionic acid (Form I);

(S)-{4-[4-(3,4-dichloro-2-methyl-phenoxy)-piperidin-1-ylmethyl]-piperidin-1-yl}-3-(4-fluoro-phenyl)-propionic acid (form II);

(2S)-2-(4-{[4-(3,4-dichloro-2-methylphenoxy)piperidin-1-yl]methyl}piperidin-1-yl)-3-(4-fluorophenyl)propanoic acid; or, (2S)-2-(4-{[4-(3,4-dichloro-2-methylphenoxy)piperidin-1-yl]methyl}piperidin-1-yl)-3-phenylpropanoic acid;
or a pharmaceutically acceptable salt thereof.

The compounds of the present invention can be prepared as described below or by methods analogous to those described in WO 2004/087659 or WO 2004/029041.

A compound of formula (I) can be prepared by reacting a compound of formula (II):

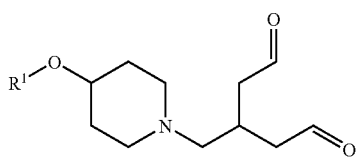

(II)

with a compound of formula (III):

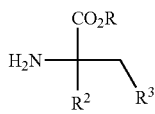

(III)

wherein R is alkyl (for example $C_{1-6}$ alkyl) in the presence of $NaBH(OAc)_3$ or $NaBH_3(CN)$ in a suitable solvent (for example an aliphatic alcohol such as methanol or ethanol) at a suitable temperature (such as in the range 0° C. to 30° C.), and subsequent ester hydrolysis by using or adapting the methods given in the Examples below.

A compound of formula (II) can be prepared by reacting a compound of formula (IV):

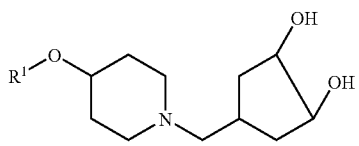

(IV)

with lead tetra-acetate in dichloromethane or sodium periodate in water.

Alternatively a compound of formula (I) wherein $R^2$ represents H may be prepared by reaction of a compound of formula (V) with a compound of formula (VI)

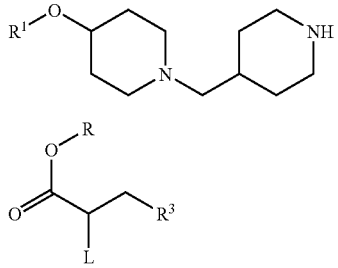

(V)

(VI)

wherein R is alkyl (for example $C_{1-6}$ alkyl) and L is a suitable leaving group (for example a sulfonate ester, typically triflate or para-nitrobenzenesulfonate), in a suitable solvent, for example dichloromethane or acetonitrile, at a temperature in the range 0-30° C. in the presence of a base, for example a tertiary amine, such as triethylamine, or an inorganic base, such as potassium carbonate; and subsequent ester hydrolysis by using or adapting the methods given in the Examples below.

The preparations of various phenoxy piperidines and other intermediates are described in the literature and in WO 01/77101, WO 2004/087659 or WO 2004/029041.

A compound of the present invention wherein R is hydrogen can be prepared by hydrolysis of the corresponding ester (prepared by a method known in the art) under standard hydrolysis conditions (for example using lithium hydroxide, sodium hydroxide, potassium hydroxide or barium hydroxide).

In the above processes it may be desirable or necessary to protect an acid group or a hydroxy or other potentially reactive group. Suitable protecting groups and details of processes for adding and removing such groups may be found in "Protective Groups in Organic Synthesis", 3rd Edition (1999) by Greene and Wuts.

In another aspect the present invention provides processes for the preparation of compounds of formula (I).

In a further aspect the invention provides the intermediates:

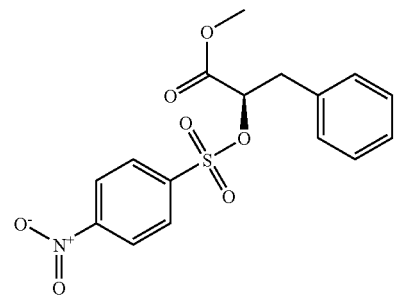

(R)-2-(4-nitro-benzenesulfonyloxy)-3-phenyl-propionic acid methyl ester

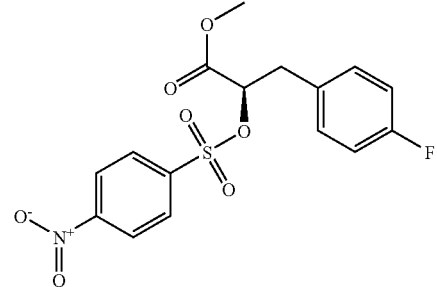

(R)-3-(4-fluoro-phenyl)-2-(4-nitro-benzene-sulfonyloxy)-propionic acid methyl ester Salts of (2S)-2-[4-[[4-(3,4-dichloro-2-methyl-phenoxy)-1-piperidyl]methyl]-1-piperidyl]-3-phenylpropanoic acid can be prepared by using or adapting the methods of the Examples or by using or adapting methods known in the art.

The compounds of the invention and their pharmaceutically acceptable salts have activity as pharmaceuticals, in particular as modulators of chemokine receptor (for example CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

Examples of these conditions are 1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus (RSV), influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis (including ulcerative colitis, microscopic colitis and indeterminant colitis), proctitis, pruritis ani; coeliac disease, irritable bowel syndrome, irritable bowel disorder, non-inflammatory diarrhoea, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumour invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins; or, 14. oncology: treatment of common cancers including prostate, breast, lung, ovarian, pancreatic, bowel and colon, stomach, skin and brain tumours and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

According to a further feature of the present invention there is provided a method for treating a chemokine mediated disease state (for example a CCR3 mediated disease state) in a mammal, such as man, suffering from, or at risk of, said disease state, which comprises administering to a mammal in need of such treatment a therapeutically effective amount of a compound of the invention or a pharmaceutically acceptable salt thereof.

According to yet another feature of the present invention there is provided a method for treating a sign and/or symptom of what is commonly referred to as a cold in a mammal, such as man, suffering from, or at risk of, said disease state, which comprises administering to a mammal in need of such treatment a therapeutically effective amount of a compound of the invention or a pharmaceutically acceptable salt thereof.

The invention also provides a compound of the invention, or a pharmaceutically acceptable salt thereof, for use in therapy.

In another aspect the invention provides the use of a compound of the invention, or a pharmaceutically acceptable salt thereof, in the manufacture of a medicament for use in therapy (for example modulating chemokine receptor activity (for example CCR3 receptor activity) or treating a sign and/or symptom of what is commonly referred to as a cold).

The invention further provides the use of a compound of the invention, or a pharmaceutically acceptable salt thereof, in the manufacture of a medicament for use in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis, rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis (including ulcerative colitis, microscopic colitis and indeterminant colitis), proctitis, pruritis ani; coeliac disease, irritable bowel syndrome, irritable bowel disorder, non-inflammatory diarrhoea, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumour invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins; or, 14. oncology: treatment of common cancers including prostate, breast, lung, ovarian, pancreatic, bowel and colon, stomach, skin and brain tumours and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; in a mammal (for example man).

In a further aspect the invention provides a compound of the invention, or a pharmaceutically acceptable salt thereof, for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}.

In a still further aspect a compound of the invention, or a pharmaceutically acceptable salt thereof, is useful in the treatment of asthma.

In another aspect a compound of the invention, or a pharmaceutically acceptable salt thereof, is useful in the treatment of respiratory syncytial virus (RSV).

The present invention also provides a the use of a compound of the invention, or a pharmaceutically acceptable salt thereof, in the manufacture of a medicament for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}.

In order to use a compound of formula (I), or a pharmaceutically acceptable salt thereof, for the therapeutic treatment of a mammal, such as man, said ingredient is normally formulated in accordance with standard pharmaceutical practice as a pharmaceutical composition. Therefore in another aspect the present invention provides a pharmaceutical composition which comprises a compound of formula (I), or a pharmaceutically acceptable salt thereof (active ingredient), and a pharmaceutically acceptable adjuvant, diluent or carrier.

In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions comprising a compound of formula (I), or a pharmaceutically acceptable salt thereof, may be administered in standard manner for the disease condition that it is desired to treat, for example by topical (such as to the lung and/or airways or to the skin), oral, rectal or parenteral (such as intravenous, sub-cutaneous, intramuscular or intra-articular) administration. For these purposes the compounds of this invention may be formulated by means known in the art. A suitable pharmaceutical composition of this invention is one suitable for oral administration in unit dosage form, for example a tablet or capsule which contains between 0.1 mg and 1 g of active ingredient.

Each patient may receive, for example, a dose of 0.01 $mgkg^{-1}$ to 100 $mgkg^{-1}$, for example in the range of 0.1 $mgkg^{-1}$ to 20 $mgkg^{-1}$, of the active ingredient administered, for example, 1 to 4 times per day.

The invention further relates to a combination therapy wherein a compound of formula (I), or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R) or T-Lymphocytes (such as CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; for example collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyran such as Zeneca ZD-2138; the compound SB-210661; a pyridinyl-substituted 2-cyanonaphthalene compound such as L-739, 010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-yls such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor, an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, levocetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agent including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a betalactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agents, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) a cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of p38; (xxv) agent modulating the function of Toll-like receptors (TLR), (xxvi) agent modulating the activity of purinergic receptors such as P2x7; (xxvii) inhibitor of transcription factor activation such as NFkB, API, or STATS; or (xxviii) a non-steroidal glucocorticoid receptor agonist.

In particular a compound of formula (I), or a pharmaceutically acceptable salt thereof, can be combined with a histamine type 1 receptor antagonist such as cetirizine, levocitirizine, loratadine, desloratadine, fexofenadine, acrivistine, azelastine, levocabastine, chlorpheniramine, promethazine, cyclizine or mizolastine; applied orally, topically or parenterally (for example orally).

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example falvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erb b2 antibody trastuzumab, or the anti-erb b1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or, (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be illustrated by the following non-limiting examples in which, unless stated otherwise:
(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 ($CD_3SOCD_3$) or $CDCl_3$ as the solvent unless otherwise stated;
(ii) mass spectra (MS) were run with an electron energy of 70 electron volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the positive mass ion-$(M+H)^+$;
(iii) the title and sub-title compounds of the examples and methods were named using either the name program from Advanced Chemistry Development Inc, version 6.00; or the index name program from Ogham with the stereochemical descriptors being added by hand (see www.eyesopen.com/products/applications/ogham.html);
(iv) unless stated otherwise, reverse phase HPLC was conducted using a "Symmetry", "NovaPak" or "Xterra" reverse phase silica column, all available from Waters Corp.;
(v) for analytical HPLC the following conditions were used:
Reverse phase analytical HPLC (Hewlett Packard Series 1100) using Waters "Symmetry" C8 column 3.5 μm; 4.6×50 mm column using 0.1% ammonium acetate/acetonitrile gradients at 2 mL/min given as % aqueous
STANDARD 75% to 5% over 3 min
FAST 45% to 5% over 2.5 min
MEDIUM FAST 65% to 5% in 2.5 min
SLOW 95% to 50% in 2.5 min
SUPERSLOW 100% to 80% in 2.5 min;
(vi) Method for X-Ray Powder Diffractometry (XRPD)
Analyses were performed on a Siemens model D5000 fitted with a position sensitive detector (PSD), a Philips X'pert Pro fitted with an X'celerator detector or a Rigaku MiniFlex X-ray powder diffractometer fitted with a scintillation detector. Samples (1-2 mg) were sprinkled on a silicon wafer zero-background holder and irradiated with copper $K_\alpha$ radiation (λ=1.54056 Å). Reflections were collected between 2.017-39.967° 2θ, typically at a step size of 0.033°2θ. Other parameters for these analyses were:
Generator=45 kV 40 mA
Scan time ~30 min
Measured time/step=200.025 sec
Divergence slit fixed=1.0
Scan axis=Gonio
PSD length=2.122
PSD mode=scanning
Incident beam monochromator
Sample=spinning
and
(v) the following abbreviations are used:

| | |
|---|---|
| RPHPLC | Reverse phase high pressure liquid chromatography |
| min | minutes |
| DMEM | tissue culture medium Dulbecco's Modified Eagles Medium |
| PSG | a combination of penicillin, streptomycin and L-glutamine |
| FCS | foetal calf serum |
| NEAA | Non-essential amino acids |
| h | hour |
| THF | Tetrahydrofuran |
| LC/MS | HPLC coupled with mass spectrometry |
| SCX | Strong cation exchange resin (Isolute SCX-2) |

PREPARATION 1

2-Chloro-4-({1-[(3,4-dihydroxycyclopentyl)methyl]piperidin-4-yl}oxy)-3-methylbenzonitrile A 2-Chloro-4-{[1-(cyclopent-3-en-1-ylmethyl)piperidin-4-yl]oxy}-3-methylbenzonitrile 2-Chloro-3-methyl-4-(piperidin-4-yloxy)benzonitrile (1.3 g) and acetic acid (0.32 ml) were combined in THF (20 ml). Sodium triacetoxyborohydride was added (1.4 g) followed by cyclopent-3-ene-1-carbaldehyde (0.62 g). The reaction was stirred for 1 h and then concentrated. The residue was partitioned between aqueous sodium bicarbonate solution and dichloromethane. The organic phase was washed with brine, dried, filtered and evaporated. The residue was purified by chromatography eluting with ethyl acetate to give the subtitle compound (1.5 g).

$^1$H NMR δ$_{(CDCl_3)}$: 1.78-1.90 (2H, m), 1.93-2.14 (4H, m), 2.28-2.39 (7H, m), 2.41-2.53 (3H, m), 2.63-2.72 (2H, m), 4.38-4.48 (1H, m), 5.64 (2H, s), 6.79 (1H, d), 7.46 (1H, d).

MS (ES+ve) 331/333 (M+H)+

Retention time (standard) 2.66

B 2-Chloro-4-({1-[(3,4-dihydroxycyclopentyl)methyl]piperidin-4-yl}oxy)-3-methylbenzonitrile 2-Chloro-4-(1-cyclopent-3-enylmethyl-piperidin-4-yloxy)-3-methyl-benzonitrile (1.5 g), potassium osmate (vi) dihydrate (0.042 g) and 4-methylmorpholine 4-oxide monohydrate (3.2 ml of a 50% soln in water) were added to acetone (40 ml) and water (5 ml). The reaction mixture was heated under reflux for 1 h. LC/MS showed complete conversion to the desired diol. The reaction was allowed to cool to room temperature and then sodium metabisulfite solution was added. The reaction mixture was extracted with dichloromethane, then sodium bicarbonate solution was added and the aqueous mixture was extracted again with dichloromethane. The organic extracts were combined and evaporated. The residue was loaded onto an SCX cartridge and eluted with dichloromethane/methanol and then with 0.7M ammonia in methanol to give the title compound (1.3 g).

$^1$H NMR $\delta_{(CDCl3)}$: 1.42-1.64 (2H, m), 1.78-2.14 (4H, m), 2.23-2.47 (9H, m), 2.51-2.86 (4H, m), 3.72 (1H, t), 3.92-4.18 (2H, m), 4.38-4.50 (1H, m), 6.78 (1H, d), 7.46 (1H, d).

MS (ES+ve) 365/367 (M+H)+

Retention time (standard) 1.53

INTERMEDIATE 1

This illustrates the preparation of methyl 2-[4-[[4-(3,4-dichloro-2-methyl-phenoxy)-1-piperidyl]methyl]-1-piperidyl]-3-(4-fluorophenyl)-propanoate 4-[4-(3,4-Dichloro-2-methyl-phenoxy)-piperidin-1-ylmethyl]-cyclopentane-1,2-diol (0.50 g) was stirred with acetic acid (0.077 ml) in water until it dissolved. Sodium periodate (0.286 g) was added and the reaction mixture was stirred, under nitrogen, for 15 min. The reaction mixture was neutralised by addition of potassium carbonate (240 mg) and product was extracted with dichloromethane. The dichloromethane was washed with brine, dried (MgSO$_4$), and filtered into a reaction flask containing 2-amino-3-(4-fluorophenyl)-propionic acid methyl ester (0.312 g), sodium triacetoxy borohydride (0.651 g) and acetic acid (0.077 ml) in dichloromethane (10 ml). The mixture was stirred at room temperature for 1 h. A saturated solution of sodium bicarbonate was added and product was extracted with dichloromethane. The dichloromethane was washed with brine, dried (MgSO$_4$), filtered and concentrated. Crude product was purified by flash chromatography eluting with ethyl acetate to give the title compound (0.52 g).

$^1$H NMR $\delta_{(CDCL3)}$: 1.08-1.29 (m, 2H), 1.41-1.63 (m, 1H), 1.69-1.86 (m, 4H), 1.90-2.00 (m, 2H), 2.14-2.39 (m, 9H), 2.57-2.68 (m, 2H), 2.82-2.95 (m, 2H), 2.97-3.09 (m, 2H), 3.39 (dd, 1H), 3.59 (s, 3H), 4.22-4.33 (m, 1H), 6.71 (d, 1H), 6.90-7.03 (m, 2H), 7.11-7.23 (m, 3H).

The following Intermediates were prepared analogously from the appropriate amino esters and diols (diols not previously described were prepared analogously to WO2004087659):

| Intermediate | Name | MS [M + H]$^+$ (ES+) | Retention time (fast gradient) | $^1$H NMR $\delta_{(CD3OD)}$ |
|---|---|---|---|---|
| 2 | Methyl (2S)-2-[4-[[4-(3,4-dichloro-2-methyl-phenoxy)-1-piperidyl]methyl]-1-piperidyl]-3-(2-methoxyphenyl)-propanoate | | 2.41 | |
| 3 | Methyl (2S)-3-(4-cyanophenyl)-2-[4-[[4-(3,4-dichloro-2-methyl-phenoxy)-1-piperidyl]methyl]-1-piperidyl]-propanoate | | | 0.97-1.14 (m, 2H), 1.37-1.52 (m, 1H), 1.58-1.76 (m, 4H), 1.84-1.95 (m, 2H), 2.10-2.15 (m, 2H), 2.16-2.39 (m, 7H), 2.53-2.63 (m, 2H), 2.73-2.81 (m, 1H), 2.89-2.99 (m, 3H), 3.35-3.42 (m, 1H), 3.50 (s, 3H), 4.27-4.37 (m, 1H), 6.81 (d, 1H), 7.17 (d, 1H), 7.30 (d, 2H), 7.53 (d, 2H) |
| 4 | Methyl (2S)-2-(4-{[4-(3,4-dichlorophenoxy)-piperidin-1-yl]methyl}piperidin-1-yl)-3-(4-fluorophenyl)-2-methylpropanoate | 537/539 | 2.23 | |
| 5 | Methyl (2S)-2-[4-[[4-(4-chloro-2-methyl-phenoxy)-1-piperidyl]methyl]-1-piperidyl]-3-(4-fluorophenyl)-2-methyl-propanoate | 517/519 | 2.20 | |
| 6 | Methyl (2S)-2-[4-[[4-(3,4-dichloro-2-methyl-phenoxy)-1-piperidyl]methyl]-1-piperidyl]-3-(4- | 551/553 | 2.54 | |

-continued

| Intermediate | Name | MS [M + H]+ (ES+) | Retention time (fast gradient) | ¹H NMR δ$_{(CD3OD)}$ |
|---|---|---|---|---|
|  | fluorophenyl)-2-methyl-propanoate |  |  |  |
| 7 | (±)-Methyl 2-[4-[[4-(3,4-dichlorophenoxy)-1-piperidyl]methyl]-1-piperidyl]-2-methyl-3-phenyl-propanoate | 519/ 521 | 2.24 |  |
| 10 | (±)-Methyl 2-[4-[[4-(3,4-dichloro-2-methyl-phenoxy)-1-piperidyl]methyl]-1-piperidyl]-2-methyl-3-phenyl-propanoate | 533/ 535 | 2.69 |  |
| 13 | Methyl (2S)-2-[4-[[4-(3,4-dichloro-2-ethyl-phenoxy)-1-piperidyl]methyl]-1-piperidyl]-3-phenylpropanoate | 533/ 535 | 2.66 |  |
| 14 | Methyl (2S)-2-[4-[[4-(3,4-dichloro-2-ethyl-phenoxy)-1-piperidyl]methyl]-1-piperidyl]-3-(4-fluorophenyl)-propanoate | 551/ 553 | 2.71 |  |
| 15 | Methyl (2S)-2-(4-{[4-(3-chloro-4-cyano-2-methylphenoxy)-piperidin-1-yl]methyl}piperidin-1-yl)-3-phenylpropanoate |  |  | 1.14-1.33 (2H, m), 1.50-1.65 (1H, m), 1.74-1.92 (4H, m), 2.00-2.11 (2H, m), 2.24-2.30 (3H, m), 2.33 (3H, s), 2.36-2.46 (3H, m), 2.64-2.74 (2H, m), 2.94-3.10 (4H, m), 3.45 (1H, dd), 3.57 (3H, s), 4.58-4.66 (1H, m), 7.09 (1H, d), 7.16-7.30 (5H, m), 7.61 (1H, d) |
| 16 | Methyl (2S)-2-(4-{[4-(3-chloro-4-cyano-2-methylphenoxy)-piperidin-1-yl]methyl}piperidin-1-yl)-3-(4-fluorophenyl)propanoate |  | 2.82 (standard gradient) | 1.08-1.29 (m, 2H), 1.41-1.63 (m, 1H), 1.69-1.86 (m, 4H), 1.90-2.00 (m, 2H), 2.14-2.39 (m, 9H), 2.57-2.68 (m, 2H), 2.82-2.95 (m, 2H), 2.97-3.09 (m, 2H), 3.39 (dd, 1H), 3.59 (s, 3H), 4.22-4.33 (m, 1H), 6.71 (d, 1H), 6.90-7.03 (m, 2H), 7.11-7.23 (m, 3H) |
| 17 | Methyl (2S)-2-[4-[[4-(2,4-dichloro-3-methyl-phenoxy)-1-piperidyl]methyl]-1-piperidyl]-3-(4-fluorophenyl)-propanoate | 537/ 539 |  | 1.12-1.32 (2H, m), 1.49-1.64 (1H, m), 1.73-1.92 (4H, m), 1.95-2.06 (2H, m), 2.25 (2H, d), 2.30-2.43 (3H, m), 2.47 (3H, s), 2.66-2.77 (2H, m), 2.89-3.06 (4H, m), 3.42 (1H, dd), 3.58 (3H, s), 3.67-3.73 (1H, m), 4.43-4.52 (1H, m), 6.94-7.07 (3H, m), 7.18-7.29 (3H, m) |
| 18 | Methyl (2S)-2-[4-[[4-(4-chloro-2-methyl-phenoxy)-1-piperidyl]methyl]-1-piperidyl]-3-(4-fluorophenyl)-propanoate |  |  | 1.11-1.33 (2H, m), 1.49-1.66 (1H, m), 1.73-1.88 (4H, m), 1.97-2.07 (2H, m), 2.20 (3H, s), 2.23-2.28 (3H, m), 2.30-2.44 (3H, m), 2.66-2.76 (2H, m), 2.91-3.08 (4H, m), 3.39-3.46 (1H, m), 3.58 (3H, s), 4.36-4.44 (1H, m), 6.89 (1H, d), 6.96-7.04 (2H, m), 7.07-7.14 (2H, m), 7.18-7.25 (2H, m) |
| 19 | Methyl (2S)-2-[4-[[4-(2,4-dichloro-phenoxy)-1-piperidyl]methyl]-1-piperidyl]-3-(4- |  |  | 1.12-1.32 (2H, m), 1.49-1.64 (1H, m), 1.73-1.91 (4H, m), 1.95-2.05 (2H, m), 2.22-2.28 (2H, m), |

| Intermediate | Name | MS [M + H]+ (ES+) | Retention time (fast gradient) | ¹H NMR δ$_{(CD3OD)}$ |
|---|---|---|---|---|
| | fluorophenyl)-propanoate | | | 2.30-2.43 (3H, m), 2.67-2.77 (2H, m), 2.90-3.07 (4H, m), 3.42 (1H, dd), 3.58 (3H, s), 3.69-3.73 (1H, m), 4.43-4.53 (1H, m), 6.96-7.11 (3H, m), 7.18-7.27 (3H, m), 7.41 (1H, d) |

INTERMEDIATES 8 & 9

This illustrates the preparation of the 2 enantiomers of methyl 2-[4-[[4-(3,4-dichlorophenoxy)-1-piperidyl]methyl]-1-piperidyl]-2-methyl-3-phenyl-propanoate (+)-Methyl 2-[4-[[4-(3,4-dichlorophenoxy)-1-piperidyl]methyl]-1-piperidyl]-2-methyl-3-phenyl-propanoate (185 mg) was eluted through a Chiralpak AD HPLC column in ethanol containing 0.1% diethylamine to give two enantiomers.

Isomer 1 (76 mg) retention time (Chiralpak AD 4.6×250 mm; 0.5 ml/min ethanol) 7.68 min.

Isomer 2 (73 mg) retention time (Chiralpak AD 4.6×250 mm; 0.5 ml/min ethanol) 9.57 min.

INTERMEDIATES 11 & 12

This illustrates the preparation of the 2 enantiomers of methyl 2-[4-[[4-(3,4-dichloro-2-methyl-phenoxy)-1-piperidyl]methyl]-1-piperidyl]-2-methyl-3-phenyl-propanoate These were prepared following the method of Intermediates 8 & 9 using (+)-methyl 2-[4-[[4-(3,4-dichloro-2-methyl-phenoxy)-1-piperidyl]methyl]-1-piperidyl]-2-methyl-3-phenyl-propanoate to give two enantiomers.

Isomer 3 retention time (Chiralpak AD 4.6×250 mm; 0.5 ml/min ethanol containing 0.1% diethylamine) 12.58 min.

Isomer 4 retention time (Chiralpak AD 4.6×250 mm; 0.5 ml/min ethanol containing 0.1% diethylamine) 15.76 min.

INTERMEDIATE 20

This illustrates the preparation of methyl 2-benzyl-2-(4-{[4-(3,4-dichlorophenoxy)piperidin-1-yl]methyl}piperidin-1-yl)butanoate This compound was prepared following the method of Example 1 using 2-amino-2-benzyl-butyric acid methyl ester and 4-[4-(3,4-dichloro-phenoxy)-piperidin-1-ylmethyl]-cyclopentane-1,2-diol.

MS (ESI+) 533/535 (M+H+)

RT (fast gradient) 2.94 min.

INTERMEDIATE 21

This illustrates the preparation of 4-(3,4-dichloro-2-methyl-phenoxy)-piperidine hydrochloride 4-Hydroxypiperidine (32.5 g) and potassium tert-butoxide (62.7 g) were added to a 1 L jacketed vessel. Tetrahydrofuran (275 mL) was added followed by N-methylpyrrolidone (25 mL). 1,2-Dichloro-4-fluoro-3-methylbenzene (50 g) in tetrahydrofuran (100 mL) was then added, followed by tetrahydrofuran (100 mL). The mixture was heated to 67° C. overnight then cooled to 50° C. Water (250 mL) was added and the mixture was stirred for 10 min at 50° C. The layers were separated and the heating was removed. The organic layer was washed with twice with 10% w/w brine (250 mL). The organic layer was heated to remove solvent by distillation firstly at atmospheric pressure and then under vacuum (400 mbar) whilst isopropanol (950 mL) was added until the tetrahydrofuran was replaced by isopropanol. The solution was then heated to 50° C. Hydrogen chloride in isopropanol (5.5M, 125 mL) was added, an exotherm to 60° C. was observed and the solution was cooled to 50° C. The mixture was cooled from 50° C. to 10° C. over 1 h and then stirred overnight at 10° C. The product was collected by filtration, washed with isopropanol (50 mL) and dried under vacuum at 40° C. to give 4-(3,4-dichloro-2-methyl-phenoxy)-piperidine hydrochloride as an off-white solid (62.3 g).

¹H NMR δ$_{(CDCL3)}$ 2.17 (2H, dd), 2.29-2.39 (2H, m), 2.34 (3H, s), 3.33 (4H, dd), 4.61-4.66 (1H, m), 6.68 (1H, d), 7.25 (1H, d), 9.64-9.83 (1H, m).

INTERMEDIATE 22

This illustrates the preparation of 4-[4-(3,4-dichloro-2-methyl-phenoxy)-piperidin-1-ylmethyl]-piperidine-1-carboxylic acid tert-butyl ester Acetonitrile (144 mL) and water (336 mL) were added to a mixture of 4-(3,4-dichloro-2-methyl-phenoxy)-piperidine hydrochloride (60 g), 4-(toluene-4-sulfonyloxymethyl)-piperidine-1-carboxylic acid tert-butyl ester (74.7 g) and potassium carbonate (57.3 g) and the mixture was heated to reflux for 7 h, then cooled over 30 min to 75° C. and held at 75° C. for 14 h, then heated over 30 min to reflux. Acetonitrile (192 mL) was added and then the mixture was cooled to 20° C. over 2 h to give a suspension. The suspension was filtered under vacuum, the filter cake was washed with water (180 mL) and then with acetonitrile (180 mL) and dried under vacuum at 40° C. to give 4-[4-(3,4-dichloro-2-methyl-phenoxy)-piperidin-1-ylmethyl]-piperidine-1-carboxylic acid tert-butyl ester as a white solid (73.9 g).

¹H NMR δ$_{(CD3OD)}$ 0.99-1.12 (2H, m), 1.45 (9H, s), 1.69-1.85 (5H, m), 1.95-2.04 (2H, m), 2.23 (2H, d), 2.31 (3H, s), 2.32-2.40 (2H, m), 2.64-2.82 (4H, m), 4.05 (2H, d), 4.38-4.46 (1H, m), 6.91 (1H, d), 7.27 (1H, d)

INTERMEDIATE 23

This illustrates the preparation of 4-[4-(3,4-dichloro-2-methyl-phenoxy)-piperidin-1-ylmethyl]-piperidine di-benzenesulfonate salt A suspension of 4-[4-(3,4-dichloro-2-methyl-phenoxy)-piperidin-1-ylmethyl]-piperidine-1-carboxylic acid tert-butyl ester (120 g) and ethanol (600 mL) were heated to 75° C. to give a solution. Benzenesulfonic acid (70% in water, 144.2 g) in ethanol (120 mL) was added dropwise over 45 min followed by a rinse with ethanol (60 mL). The solution was heated at 75° C. for 1 h and was then cooled to 20° C. over 1 h 45 min. The resultant solid was collected, the filter cake was washed with ethanol (480 mL) then dried under vacuum overnight at 40° C. to give 4-[4-(3,4-dichloro-2-methyl-phenoxy)-piperidin-1-ylmethyl]-piperidine di-benzenesulfonate salt as a white solid (161.9 g).

$^1$H NMR $\delta_{(DMSO)}$ 1.3-1.41 (2H, m), 1.89-1.93 (3H, m), 2.02-2.15, (4H, m), 2.25, s and 2.34 (3H, s), 2.83-2.94 (2H, m), 3.06-3.12, (4H, m), 3.28-3.36, (2H, m), 3.45-3.49, (1H, m), 3.58-3.62 (1H, m) 4.5-4.65 and 4.78-4.84 (2×m, 1H) 7.09 and 7.14 (2×d, 1H), 7.3-7.37, (6H, m), 7.45 (1H, d); 7.59-7.63 (4H, m), 8.23 (1H, br s), 8.49 (1H, br s), 8.98 (1H, br s).

INTERMEDIATE 24

This illustrates the preparation of (R)-2-(4-nitro-benzenesulfonyloxy)-3-phenyl-propionic acid methyl ester Toluene (160 mL) was added to (R)-3-phenyllacetic acid, methyl ester (20 g) and p-nitrobenzenesulfonyl chloride (25.8 g) to give a clear yellow solution which was cooled to 0° C. Triethylamine (16.4 mL) was added over 15 min, the mixture was stirred at 3° C. for 2 h and then overnight at room temperature. Water (120 mL) was added and the reaction mixture stirred at RT for 1 h. The layers were separated and the organic layer was washed with water (120 mL). Toluene (20 mL) was added to the resulting organic layer and the solution was heated to remove solvent by distillation under vacuum (60 mbar) to leave 140 mL solvent in the vessel. Isohexane (120 mL) was added at 40° C. and the mixture was stirred at this temperature overnight. The mixture was then cooled to 25° C. over 115 min and was then filtered. The filter cake was washed with toluene (20 mL) and isohexane (20 mL), then dried under vacuum at 40° C. to give (R)-2-(4-nitro-benzenesulfonyloxy)-3-phenyl-propionic acid methyl ester as a cream solid (31.6 g).

$^1$H NMR $\delta_{(CDCl3)}$ 3.0-3.08 (1H, dd), 3.2-3.26 (1H, dd), 3.78 (3H, s), 5.0-5.04 (1H, dd), 7.02-7.06 (2H, m), 7.12-7.2 (3H, m), 7.73-7.78 (2H, d), 8.13-8.18 (2H, d).

INTERMEDIATE 25

This illustrates the preparation of (R)-3-(4-fluoro-phenyl)-2-(4-nitro-benzenesulfonyloxy)-propionic acid methyl ester (R)-3-(4-Fluorophenyl)-2-hydroxypropionic acid methyl ester (20 g) and 4-nitrobenzenesulfonyl chloride (22.8 g) were dissolved in methylisobutyl ketone (240 mL). The solution was cooled to 0-5° C. and triethylamine (10.74 g) was added dropwise over 15 min. The reaction mixture was stirred at 0-5° C. for 2 hours. Water (80 mL) was added and the mixture heated to 35-40° C. to obtain a clear biphasic solution. The aqueous layer was removed and the organic phase washed successively with dilute hydrochloric acid (1M, 80 mL) and then water at 35-40° C. The organic phase was concentrated by distillation under reduced pressure at 35-40° C. to a final volume of about 120 mL. To the resulting slurry of the product was added isohexane (120 mL) and the mixture cooled to 0-5° C. for 2 h. The solid was filtered, washed with isohexane (60 mL) and then dried in a vacuum oven at 40° C. under reduced pressure to yield the title compound as a yellow solid (32.64 g).

$^1$H NMR $\delta_{(CDCl3)}$ 3.02-3.10 (1H, dd), 3.18-3.24 (1H, dd), 3.73 (3H, s), 6.85-6.91 (2H, m), 7.03-7.07 (2H, m), 7.86 (2H, d), 8.25 (2H, d).

INTERMEDIATE 26

This illustrates the preparation of (S)-2-{4-[4-(3,4-dichloro-2-methyl-phenoxy)-piperidin-1-ylmethyl]-piperidin-1-yl}-3-phenyl-propionic acid methyl ester Water (90 mL) was added to 4-[4-(3,4-dichloro-2-methyl-phenoxy)-piperidin-1-ylmethyl]-piperidine di-benzenesulfonate salt (30 g) to give a suspension. The suspension was stirred at room temperature for 2 min to give a clear solution. Tert-butyl methyl ether (150 mL) was then charged in one portion and the vessel contents were warmed to 30° C. A solution of 10M Sodium Hydroxide (13.9 g) in water (90 mL) was added over 2 min and the solution was stirred at 30° C. for 10 min then the layers were separated. The organic layer was evaporated to dryness, acetonitrile (100 mL) was added and the evaporation was continued until the volume equalled 80 mL. Acetonitrile (70 mL) was then added and to this solution was added potassium carbonate (7.8 g) followed by a solution of (R)-2-(4-nitro-benzenesulfonyloxy)-3-phenyl-propionic acid methyl ester (16.3 g) in acetonitrile (30 mL). The resulting suspension was heated to 60° C. and held at this temperature overnight. The mixture was cooled to 20° C. then tert-butyl methyl ether (150 mL) was added. The suspension was filtered and the vessel and cake were washed with tert-butyl methyl ether (30 mL). The filtrate was washed with 5% brine (90 mL). The layers were separated and the organic layer was washed with ammonium acetate/acetic acid solution (72 mL; 15 g Ammonium acetate in 1 L 0.5 M aqueous acetic acid) at 25° C. and then warmed to 40° C. whereupon hydrochloric acid (1M, 90 mL) was added. The layers were separated, the organic layer was re-extracted with hydrochloric acid (1M, 30 mL) and then the aqueous phases were combined. Tert-butyl methyl ether (150 mL) and 2M Sodium Hydroxide (90 mL) were added and the mixture stirred at 40° C. for 10 min before the phases were separated. The organic phase was reduced in vacuo to a low volume then ethanol (120 mL) was added and distillation was continued for a short time till some of the ethanol had been removed. Ethanol (5 mL) was added to the residue (volume 90 mL) and the solution seeded with (S)-2-{4-[4-(3,4-Dichloro-2-methyl-phenoxy)-piperidin-1-ylmethyl]-piperidin-1-yl}-3-phenyl-propionic acid methyl ester (50 mg) and the mixture was cooled to 5° C. over 3 h. A colourless solid was collected by filtration, the cake was washed with ethanol (15 mL) and the solid dried under vacuum at 35° C. overnight to give the title compound (16.3 g).

INTERMEDIATE 27

This illustrates the preparation of (S)-{4-[4-(3,4-dichloro-2-methyl-phenoxy)-piperidin-1-ylmethyl]-piperidin-1-yl}-3-(4-fluoro-phenyl)-propionic acid methyl ester 4-[4-(3,4-Dichloro-2-methyl-phenoxy)-piperidin-1-ylmethyl]-piperidine di-benzenesulfonate salt (40 g) was dissolved in water (120 mL). To the stirred solution was added methyl t-butylether (320 mL), followed by a solution of sodium hydroxide (10M, 22.25 mL) in water (120 mL). The solution was heated at 25-30° C. for 20 minutes. The organic layer was separated from the aqueous and about 200 mL of the solvent was removed by distillation at atmospheric pressure. To the residue was added acetonitrile (200 mL) and further solvent removed by distillation to a final volume of about 240 mL. Karl-Fisher analysis of this solution indicated 0.35% w/w water was present. To this solution of the free base in acetonitrile was added potassium carbonate (10.40 g) and a solution of 3-(4-fluorophenyl)-2-(4-nitrobenzenesulfonyloxy)-propionic acid methyl ester (22.80 g) in acetonitrile (24 mL—prepared by heating the acetonitrile to 35° C.). A small amount of solid residue was washed in with acetonitrile (16 mL). The reaction mixture was heated at 60-65° C. for 16 h, then cooled to room temperature and methyl t-butylether (200 mL) added. After stirring at room temperature for 20 minutes, the precipitated salts were filtered and washed with methyl t-butylether (40 mL). The filtrate was stirred successively with sodium chloride solution (5% w/v in water, 120 mL), ammonium acetate solution (96 mL, 0.2M ammonium acetate in 0.5M aqueous acetic acid solution) and sodium chloride solution (5% w/v, 120 mL), each for 10 minutes. The organic layer was separated and solvent distilled off to a final volume of about 120 mL. To the residue was added acetonitrile (120 mL) and the volume reduced to about 120 mL (the final distillate temperature was 78-80° C.). The residue was diluted with acetonitrile (120 mL). A sample was withdrawn and evaporated and weighed to indicate that this solution contained about 33 g of the title compound in 240 mL of acetonitrile.

$^1$H NMR $\delta_{(CDCl3)}$ 1.18-2.30 (2H, m), 1.4-1.56 (1H, m), 1.74-1.90 (4H, m), 1.90-1.93 (2H, m), 2.13-2.25 (5H, m), 2.3-2.4 (4H, m), 2.6-2.7 (2H, m), 2.8-2.98 (2H, m), 2.98-3.10 (2H, m), 3.35-3.41 (1H, m), 3.6 (3H, s), 4.25-4.35 (1H, s), 6.9-6.70 (1H, d), 6.91-6.97 (2H, m), 7.12-7.26 (3H, m).

MS (ES+ve) 537 (M+H)+

INTERMEDIATE 28

This illustrates the preparation of 4-{[4-(4-Chloro-2-methylphenoxy)piperidin-1-yl]methyl}cyclopentane-1,2-diol a) 4-(4-Chloro-2-methylphenoxy)-1-(cyclopent-3-en-1-ylcarbonyl)piperidine 4-(4-Chloro-2-methylphenoxy)piperidine hydrochloride (28.6 g) and triethylamine (45.5 mL) were stirred in dichloromethane (100 mL) and cyclopent-3-ene-1-carbonyl chloride (14.26 g) in dichloromethane (100 mL) was added dropwise. When addition was complete, the reaction mixture was stirred at room temperature for 2 h. Water (250 mL) was added to the reaction mixture and product was extracted with dichloromethane. The dichloromethane was washed with brine, dried (MgSO$_4$), filtered and concentrated in vacuo. The crude product was filtered through a plug of silica eluting with diethyl ether to give the subtitle compound (29.5 g).

Retention Time (standard): 2.63
MS (ES+): 320/322 [M+H]$^+$
$^1$H NMR $\delta_{(CDCL3)}$ 1.76-1.98 (4H, m), 2.21 (3H, s), 2.53-2.64 (2H, m), 2.69-2.77 (2H, m), 3.29-3.38 (1H, m), 3.46-3.54 (1H, m), 3.68-3.77 (3H, m), 4.49-4.56 (1H, m), 5.68 (2H, d), 6.75 (1H, d), 7.06-7.15 (2H, m)

b) 4-{[4-(4-Chloro-2-methylphenoxy)piperidin-1-yl]carbonyl}cyclopentane-1,2-diol 4-(4-Chloro-2-methylphenoxy)-1-(cyclopent-3-en-1-ylcarbonyl)piperidine (29.5 g), N-methylmorpholine-N-oxide (37 g) and potassium osmate dihydrate (0.85 g) were stirred in a mixture of acetone (200 mL) and water (50 mL) overnight. A saturated solution of sodium metabisulphite (200 mL) was added and the mixture was stirred for 15 min. Product was extracted with dichloromethane. The dichloromethane was washed with ammonium chloride solution then with brine, dried (MgSO$_4$), filtered and concentrated in vacuo to give the subtitle compound (32.0 g) as a mixture of 2 stereoisomers.

Retention Time (standard) 1.74 and 1.85 min MS (ES+) 354/356 [M+H]$^+$; base peak: 226 c) 4-{[4-(4-Chloro-2-methylphenoxy)piperidin-1-yl]methyl}cyclopentane-1,2-diol 4-{[4-(4-Chloro-2-methylphenoxy)piperidin-1-yl]carbonyl}cyclopentane-1,2-diol (32.0 g) was dissolved in tetrahydrofuran (100 mL) and stirred, at room temperature, under nitrogen. Borane (1 M solution in THF; 300 mL) was added dropwise and then the reaction mixture was heated under reflux for 2 h. The reaction mixture was allowed to cool slightly and methanol (60 mL) was added carefully. Heating was resumed and continued overnight. The reaction mixture was concentrated in vacuo and the residue was purified using SCX resin:Non-basic impurities were eluted with methanol then product was eluted with 0.7 M ammonia in methanol. Solvent was removed in vacuo to give the title compound (30 g) as a mixture of 2 stereoisomers.

Retention Time (standard) 1.51
MS (ES+) 340/342 [M+H]$^+$

INTERMEDIATE 29

This illustrates the preparation of methyl (2S)-2-(4-{[4-(4-chloro-2-methylphenoxy)piperidin-1-yl]methyl}piperidin-1-yl)-3-(4-fluorophenyl)-2-methylpropanoate 4-{[4-(4-Chloro-2-methylphenoxy)piperidin-1-yl]methyl}cyclopentane-1,2-diol (13.18 g) was dissolved in water (85 ml). Acetic acid (2.22 ml) and sodium periodate (8.38 g) were added. The mixture was then stirred under nitrogen for 30 min. Potassium carbonate (6.97 g) was added and the solution was diluted with water and extracted into chloroform (210 ml) and then dichloromethane (2×120 ml). The combined extracts were washed with brine, dried over magnesium sulfate and then poured directly into a solution of methyl 4-fluoro-α-methyl-L-phenylalaninate (8.196 g), sodium triacetoxyborohydride (18.91 g) and acetic acid (2.22 ml) in dichloromethane (35 ml). The resultant mixture was stirred under nitrogen for 1 h. The solution was poured into saturated sodium bicarbonate solution (1 l). The mixture was extracted with dichloromethane (3×500 ml). The extracts were dried over magnesium sulfate and evaporated in vacuo. The crude material was purified by chromatography on neutral alumina (wetted with 5% water, 1 kg) eluting with 1:1 isohexane:ethyl acetate to give the subtitle compound (15.5 g) as an oil.

MS ESI (+ve) 517/519 (M+H)$^+$
Retention Time (fast gradient) 2.03 min.

INTERMEDIATE 30

This illustrates the preparation of methyl (2R)-2-(4-{[4-(4-chloro-2-methylphenoxy)piperidin-1-yl]methyl}piperidin-1-yl)-3-(4-fluorophenyl)-2-methylpropanoate Prepared following the method of Intermediate 29 using methyl 4-fluoro-α-methyl-R-phenylalaninate.

MS ESI (+ve) 517/519 (M+H)$^+$
Retention Time (fast gradient) 2.24 min.

EXAMPLE 1

This Example illustrates the preparation of (2S)-2-[4-[[4-(3,4-dichloro-2-methyl-phenoxy)-1-piperidyl]methyl]-1-piperidyl]-3-(4-fluorophenyl)-propanoic acid A solution of lithium hydroxide monohydrate (0.162 g) in water was added to a stirred solution of 2-{4-[4-(3,4-dichloro-2-methyl-phenoxy)-piperidin-1-ylmethyl]-piperidin-1-yl}-3-(4-fluoro-phenyl)-propionic acid methyl ester (0.52 g) in tetrahydrofuran (6 ml) and methanol (2 ml). The mixture was stirred at room temperature overnight. Ammonium acetate (3 g) in water (5 mL) was added followed by ether (10 mL). The mixture was stirred for 1 h then a white solid was collected by filtration. 100 mg was further purified by RP HPLC (gradient ammonium acetate:acetonitrile 95:5-5:95) to give the title compound (80 mg).

MS [M−H]⁻ (APCI−) 521/523

Retention time (standard) 1.89

¹H NMR δ$_{(CD3OD)}$: 1.15-1.39 (2H, m), 1.51-1.66 (1H, m), 1.74-1.88 (4H, m), 1.95-2.08 (2H, m), 2.25 (2H, d), 2.31-2.45 (7H, m), 2.64-2.74 (2H, m), 2.84 (1H, dd), 2.98-3.12 (3H, m), 3.17 (1H, dd), 4.39-4.49 (1H, m), 6.90-6.98 (3H, m), 7.23-7.32 (3H, m).

The following compounds were prepared from the corresponding ester using the method of Example 1:

| Example | Name | MS [M + H]⁺ (APCI+) | ¹H NMR δ$_{(CD3OD)}$ |
|---|---|---|---|
| 2 | (2S)-2-[4-[[4-(3,4-dichloro-2-methyl-phenoxy)-1-piperidyl]methyl]-1-piperidyl]-3-(2-methoxyphenyl)-propanoic acid | 535/537 | 1.15-1.41 (2H, m), 1.50-1.66 (1H, m), 1.72-1.88 (4H, m), 1.95-2.06 (2H, m), 2.25 (2H, d), 2.30-2.45 (7H, m), 2.63-2.75 (2H, m), 2.90 (1H, t), 3.02-3.14 (3H, m), 3.25-3.37 (1H, m), 3.83 (3H, s), 4.38-4.48 (1H, m), 6.80 (1H, t), 6.90 (2H, dd), 7.13 (1H, t), 7.22-7.31 (2H, m). |
| 3 | (2S)-3-(4-cyanophenyl)-2-[4-[[4-(3,4-dichloro-2-methyl-phenoxy)-1-piperidyl]methyl]-1-piperidyl]-propanoic acid | 530/532 | 1.15-1.36 (2H, m), 1.51-1.66 (1H, m), 1.74-1.88 (4H, m), 1.96-2.07 (2H, m), 2.25 (2H, d), 2.31-2.46 (7H, m), 2.64-2.74 (2H, m), 2.93-3.22 (5H, m), 4.39-4.49 (1H, m), 6.93 (1H, d), 7.29 (1H, dd), 7.47 (2H, d), 7.60 (2H, dd) |
| 13 | (2S)-2-[4-[[4-(3,4-dichloro-2-ethyl-phenoxy)-1-piperidyl]methyl]-1-piperidyl]-3-phenylpropanoic acid | 519/521 | 1.12 (3H, t), 1.16-1.37 (2H, m), 1.48-1.63 (1H, m), 1.71-1.86 (4H, m), 1.96-2.05 (2H, m), 2.23 (2H, d), 2.31-2.44 (4H, m), 2.63-2.72 (2H, m), 2.76-2.90 (3H, m), 2.94-3.03 (1H, m), 3.04-3.14 (2H, m), 3.18-3.25 (1H, m), 4.39-4.48 (1H, m), 6.90 (1H, d), 7.07-7.13 (1H, m), 7.19 (2H, t), 7.23-7.29 (3H, m) |
| 14 | (2S)-2-[4-[[4-(3,4-dichloro-2-ethyl-phenoxy)-1-piperidyl]methyl]-1-piperidyl]-3-(4-fluorophenyl)-propanoic acid | 537/539 | 1.11 (3H, t), 1.16-1.35 (2H, m), 1.50-1.62 (1H, m), 1.71-1.86 (4H, m), 1.96-2.05 (2H, m), 2.23 (2H, d), 2.30-2.43 (4H, m), 2.62-2.71 (2H, m), 2.75-2.90 (3H, m), 2.95-3.09 (3H, m), 3.11-3.19 (1H, m), 4.39-4.47 (1H, m), 6.87-6.95 (3H, m), 7.22-7.28 (3H, m) |
| 15 | (22S)-2-(4-{[4-(3-chloro-4-cyano-2-methylphenoxy)-piperidin-1-yl]methyl}piperidin-1-yl)-3-phenylpropanoic acid | 494/ 496 (M − H, ES−) | 1.16-1.39 (2H, m), 1.51-1.67 (1H, m), 1.74-1.93 (4H, m), 2.00-2.11 (2H, m), 2.26 (2H, d), 2.33 (3H, s), 2.35-2.47 (4H, m), 2.64-2.73 (2H, m), 2.85 (1H, dd), 2.99-3.16 (3H, m), 3.23 (1H, dd), 4.57-4.67 (1H, m), 7.07-7.17 (2H, m), 7.19-7.31 (4H, m), 7.62 (1H, d) |
| 16 | (2S)-2-(4-{[4-(3-chloro-4-cyano-2-methylphenoxy)-piperidin-1-yl]methyl}piperidin-1-yl)-3-(4-fluorophenyl)-propanoic acid | 514/516 | 1.13-1.32 (2H, m), 1.49-1.63 (1H, m), 1.74-1.91 (4H, m), 2.00-2.11 (2H, m), 2.25 (3H, d), 2.33 (3H, s), 2.37-2.45 (3H, m), 2.63-2.74 (2H, m), 2.91-3.08 (4H, m), 3.43 (1H, dd), 3.58 (3H, s), 4.56-4.66 (1H, m), 6.96-7.04 (2H, m), 7.09 (1H, d), 7.19-7.24 (2H, m), 7.61 (1H, d) |
| 17 | (2S)-2-[4-[[4-(2,4-dichloro-3-methyl-phenoxy)-1-piperidyl]methyl]-1-piperidyl]-3-(4-fluorophenyl)-propanoic acid | 523/525 | 1.16-1.39 (2H, m), 1.51-1.67 (1H, m), 1.74-1.91 (4H, m), 1.95-2.06 (2H, m), 2.25 (2H, d), 2.31-2.43 (4H, m), 2.45 (3H, s), 2.66-2.76 (2H, m), 2.81-2.89 (1H, m), 3.00-3.18 (4H, m), 4.42-4.51 (1H, m), 6.94 (3H, t), 7.24-7.30 (3H, m) |
| 18 | (2S)-2-[4-[[4-(4-chloro-2-methyl-phenoxy)-1-piperidyl]methyl]-1-piperidyl]-3-(4-fluorophenyl)-propanoic acid | 489/491 | 1.16-1.39 (2H, m), 1.50-1.64 (1H, m), 1.75-1.87 (4H, m), 1.96-2.07 (2H, m), 2.19 (3H, s), 2.25 (2H, d), 2.30-2.42 (4H, m), 2.64-2.74 (2H, m), 2.86 (1H, dd), 3.00-3.17 (4H, m), 4.35-4.44 (1H, m), 6.86-6.97 (3H, m), 7.07-7.12 (2H, m), 7.24-7.30 (2H, m) |
| 19 | (2S)-2-[4-[[4-(2,4-dichloro-phenoxy)-1-piperidyl]methyl]-1- | 509/511 | 1.16-1.39 (2H, m), 1.51-1.67 (1H, m), 1.74-1.91 (4H, m), 1.96-2.07 (2H, m), 2.26 (2H, d), 2.33-2.44 (4H, |

| Example | Name | MS [M + H]+ (APCI+) | $^1$H NMR $\delta_{(CD3OD)}$ |
|---------|------|---------------------|------------------------------|
|         | piperidyl]-3-(4-fluorophenyl)-propanoic acid | | m), 2.66-2.76 (2H, m), 2.87 (1H, d), 3.06 (3H, t), 3.15 (1H, d), 4.44-4.54 (1H, m), 6.94 (2H, t), 7.10 (1H, d), 7.23-7.31 (3H, m), 7.40 (1H, dd) |

EXAMPLE 4

This Example illustrates the preparation of (s)-2-(4-{[4-(3,4-dichlorophenoxy)piperidin-1-yl]methyl}piperidin-1-yl)-3-(4-fluorophenyl)-2-methylpropanoic acid A mixture of methyl (S)-2-(4-{[4-(3,4-dichlorophenoxy)piperidin-1-yl]methyl}piperidin-1-yl)-3-(4-fluorophenyl)-2-methylpropanoate (123 mg), barium hydroxide (130 mg), tetrahydrofuran (2 ml), water (1 ml) and methanol (1 ml) were heated together in the microwave at 190° C. for 2.5 h. The mixture was then acidified with acetic acid (1 ml), concentrated, and purified by reverse-phase hplc (95:5 0.1% aqueous ammonium acetate/acetonitrile to 5:95 0.1% aqueous ammonium acetate/acetonitrile over 10 minutes, symmetry column to give the title compound (109 mg).

$^1$H NMR $\delta_{(CD3OD)}$ 1.00 (3H, s), 1.18-1.35 (2H, m), 1.48-1.62 (1H, m), 1.70-1.81 (4H, m), 1.94-2.04 (2H, m), 2.16-2.45 (6H, m), 2.71 (3H, d), 3.03-3.16 (2H, m), 3.23 (1H, d), 4.32-4.43 (1H, m), 6.89 (3H, t), 7.08 (1H, d), 7.25 (2H, t), 7.37 (1H, d).

MS (ES+ve) 523/525 (M+H)+

The following compounds were prepared from the corresponding ester using the method of Example 4:

| Example | Name | MS [M + H]+ (APCI+) | $^1$H NMR $\delta_{(CD3OD)}$ |
|---------|------|---------------------|------------------------------|
| 5 | (S)-2-[4-[[4-(4-chloro-2-methyl-phenoxy)-1-piperidyl]methyl]-1-piperidyl]-3-(4-fluorophenyl)-2-methyl-propanoic acid | 503/505 | 1.00 (3H, s), 1.20-1.36 (2H, m), 1.50-1.63 (1H, m), 1.71-1.85 (4H, m), 1.94-2.04 (2H, m), 2.17 (3H, s), 2.19-2.25 (3H, m), 2.29-2.44 (3H, m), 2.63-2.74 (3H, m), 3.03-3.16 (2H, m), 3.22 (1H, d), 4.33-4.42 (1H, m), 6.85-6.92 (3H, m), 7.05-7.10 (2H, m), 7.25 (2H, dd) |
| 6 | (S)-2-[4-[[4-(3,4-dichloro-2-methyl-phenoxy)-1-piperidyl]methyl]-1-piperidyl]-3-(4-fluorophenyl)-2-methyl-propanoic acid | 537/539 | 1.00 (3H, s), 1.21-1.36 (2H, m), 1.49-1.63 (1H, m), 1.71-1.86 (4H, m), 1.95-2.06 (2H, m), 2.16-2.26 (3H, m), 2.28-2.44 (3H, m), 2.31 (3H, s), 2.62-2.75 (3H, m), 3.02-3.17 (2H, m), 3.22 (1H, d), 4.37-4.46 (1H, m), 6.85-6.93 (3H, m), 7.21-7.29 (3H, m) |
| 12 | Isomer 4 of 2-[4-[[4-(3,4-dichloro-2-methyl-phenoxy)-1-piperidyl]methyl]-1-piperidyl]-2-methyl-3-phenyl-propanoic acid | 519/521 | 0.96 (3H, d), 1.15-1.33 (2H, m), 1.44-1.59 (1H, m), 1.66-1.82 (4H, m), 1.89-2.02 (2H, m), 2.08-2.43 (9H, m), 2.56-2.72 (4H, m), 3.05 (2H, d), 4.32-4.43 (1H, m), 6.83-6.91 (1H, m), 7.02-7.16 (3H, m), 7.17-7.27 (3H, m) |

EXAMPLE 11

This Example illustrates the preparation of Isomer 3 of 2-(4-{[4-(3,4-dichloro-2-methylphenoxy)piperidin-1-yl]methyl}piperidin-1-yl)-2-methyl-3-phenylpropanoic acid.

Methyl 2-(4-{[4-(3,4-dichloro-2-methylphenoxy)piperidin-1-yl]methyl}piperidin-1-yl)-2-methyl-3-phenylpropanoate (Isomer 3; 177 mg), 6M hydrochloric acid (20 ml) and isopropyl alcohol (10 ml) were heated together at 98° C. for 22 days. The mixture was then cooled, concentrated and purified by reverse-phase hplc using 95:5 0.1% aqueous ammonium acetate/acetonitrile to 5:95 0.1% aqueous ammonium acetate/acetonitrile over minutes, symmetry column, to give the title compound (38 mg).

MS [M–H]– 519/521 (APCI–)

$^1$H NMR $\delta_{(CD3OD)}$: 1.01 (3H, s), 1.24-1.35 (2H, m), 1.50-1.62 (1H, m), 1.71-1.87 (4H, m), 1.96-2.05 (2H, m), 2.15-2.26 (4H, m), 2.30 (3H, s), 2.32-2.43 (2H, m), 2.61-2.75 (3H, m), 3.01-3.18 (2H, m), 3.25 (1H, d), 4.38-4.46 (1H, m), 6.91 (1H, d), 7.08-7.29 (6H, m).

The following compounds were prepared from the corresponding ester using the method of Example 11:

| Example | Name | MS [M + H]+ (APCI+) | $^1$H NMR $\delta_{(CD3OD)}$ |
|---|---|---|---|
| 8 | Isomer 1 of 2-[4-[[4-(3,4-dichlorophenoxy)-1-piperidyl]methyl]-1-piperidyl]-2-methyl-3-phenyl-propanoic acid | 505/507 | 1.01 (3H, s), 1.17-1.37 (2H, m), 1.50-1.62 (1H, m), 1.70-1.82 (4H, m), 1.94-2.06 (2H, m), 2.15-2.47 (6H, m), 2.66-2.76 (4H, m), 3.05-3.18 (2H, m), 4.34-4.42 (1H, m), 6.88 (1H, dd), 7.07-7.13 (2H, m), 7.17 (2H, t), 7.25 (2H, d), 7.37 (1H, d) |
| 9 | Isomer 2 of 2-[4-[[4-(3,4-dichlorophenoxy)-1-piperidyl]methyl]-1-piperidyl]-2-methyl-3-phenyl-propanoic acid | 505/507 | 1.01 (3H, s), 1.19-1.36 (2H, m), 1.50-1.63 (1H, m), 1.76 (4H, d), 1.95-2.04 (2H, m), 2.16-2.26 (4H, m), 2.31 (2H, t), 2.43 (1H, t), 2.65-2.76 (3H, m), 3.13 (2H, t), 4.34-4.43 (1H, m), 6.87-6.90 (1H, m), 7.08-7.13 (2H, m), 7.17 (2H, t), 7.25 (2H, d), 7.37 (1H, d) |
| 10 | (±)-2-[4-[[4-(3,4-dichloro-2-methyl-phenoxy)-1-piperidyl]methyl]-1-piperidyl]-2-methyl-3-phenyl-propanoic acid | 519/521 | 1.01 (3H, s), 1.24-1.35 (2H, m), 1.50-1.62 (1H, m), 1.71-1.87 (4H, m), 1.96-2.05 (2H, m), 2.15-2.26 (4H, m), 2.30 (3H, s), 2.32-2.43 (2H, m), 2.61-2.75 (3H, m), 3.01-3.18 (2H, m), 3.25 (1H, d), 4.38-4.46 (1H, m), 6.91 (1H, d), 7.08-7.29 (6H, m) |

EXAMPLE 20

This Example illustrates the preparation of (2S)-2-[4-[[4-(3,4-dichloro-2-methyl-phenoxy)-1-piperidyl]methyl]-1-piperidyl]-3-phenylpropanoic acid sodium salt (2S)-2-[4-[[4-(3,4-Dichloro-2-methyl-phenoxy)-1-piperidyl]methyl]-1-piperidyl]-3-phenylpropanoic acid (1.0 g) was suspended in methanol. Sodium hydroxide (79 mg) in water (1 ml) was added and the resulting solution was stirred for 1 h and then the solvent was evaporated. The residue was dissolved in ethanol (50 ml) at reflux and then allowed to cool. The volume was reduced to 30 ml by evaporation and the resulting solution was left to crystallise overnight. Collection of the resultant crystals gave the title compound (0.6 g).

Melting point: 227-229° C.

2.48% water by Karl Fisher analysis $^1$H NMR $\delta_{(CD3OD)}$: 1.10-1.26 (2H, m), 1.43-1.53 (1H, m), 1.62-1.75 (4H, m), 1.85-1.95 (2H, m), 2.13 (2H, d), 2.21 (3H, s), 2.18-2.27 (2H, m), 2.33 (2H, t), 2.53-2.62 ((2H, m), 2.67-2.75 (1H, m), 2.86-2.95 (1H, m), 2.96-3.07 (2H, m), 3.11-3.17 (1H, m), 4.26-4.36 (1H, m), 6.81 (1H, d), 7.01 (1H, t), 7.10 (2H, t), 7.13-7.20 (3H, m).

EXAMPLE 21

This Example illustrates the preparation of (2S)-2-[4-[[4-(3,4-dichloro-2-methyl-phenoxy)-1-piperidyl]methyl]-1-piperidyl]-3-(4-fluorophenyl)-propanoic acid sodium salt This compound was prepared following the method of Example 20 using (2S)-2-[4-[[4-(3,4-dichloro-2-methyl-phenoxy)-1-piperidyl]methyl]-1-piperidyl]-3-(4-fluorophenyl)-propanoic acid and recrystallising by stirring with isopropanol.

Melting point: 230-232° C.

$^1$H NMR $\delta_{(CD3OD)}$ 1.13-1.40 (2H, m), 1.53-1.68 (1H, m), 1.75-1.89 (4H, m), 1.96-2.08 (2H, m), 2.25 (2H, d), 2.31-2.50 (7H, m), 2.66-2.75 (2H, m), 2.82 (1H, dd), 2.98-3.15 (3H, m), 3.22 (1H, dd), 4.38-4.49 (1H, m), 6.91-7.00 (3H, m), 7.25-7.32 (3H, m).

EXAMPLE 22

This Example illustrates the preparation of (2S)-2-[4-[[4-(3,4-dichloro-2-methyl-phenoxy)-1-piperidyl]methyl]-1-piperidyl]-3-(4-fluorophenyl)-propanoic acid potassium salt This compound was prepared following the method of Example 20 using (2S)-2-[4-[[4-(3,4-dichloro-2-methyl-phenoxy)-1-piperidyl]methyl]-1-piperidyl]-3-(4-fluorophenyl)-propanoic acid and potassium hydroxide. The initial product from evaporation of the solvent was resuspended in methanol and evaporated and then suspended in diethyl ether and evaporated to give the title compound.

Melting point: 210-214° C.

EXAMPLE 23

This Example illustrates the preparation of (2S)-2-[4-[[4-(3,4-dichloro-2-methyl-phenoxy)-1-piperidyl]methyl]-1-piperidyl]-3-phenylpropanoic acid methanesulfonic acid salt (2S)-2-[4-[[4-(3,4-Dichloro-2-methyl-phenoxy)-1-piperidyl]methyl]-1-piperidyl]-3-phenylpropanoic acid (1.0 g) was suspended in methanol-water (3:1, 30 mL). Methanesulfonic acid (190 mg) was added and the mixture was heated under reflux until solution was obtained. The solution was cooled and the solvent was evaporated. Recrystallisation from ethanol gave the title compound (0.9 g)

Melting point: 225-228° C.

3.09% water by Karl Fisher analysis $^1$H NMR $\delta_{(CD3OD)}$ 1.54-1.71 ((2H, m), 2.00-2.29 (7H, m), 2.35 (3H, s), 2.70 (3H, s), 2.98-3.07 (2H, m), 3.10 (2H, d), 3.23 (2H, d), 3.27-3.43 (4H, m), 3.53 (1H, d), 3.65 (1H, d), 3.75-3.84 (1H, m), 4.63-4.73 (1H, m), 6.96 (1H, d), 7.20-7.26 (1H, m), 7.26-7.39 (5H, m).

EXAMPLE 24

This Example illustrates the preparation of (2S)-2-[4-[[4-(3,4-dichloro-2-methyl-phenoxy)-1-piperidyl]methyl]-1-piperidyl]-3-phenylpropanoic acid benzenesulfonic acid salt This compound was prepared following the method of Example 23 using benzenesulfonic acid. The salt crystallised directly on cooling the initial solution.

Melting point: 160-162° C.

2.4% water by Karl Fisher analysis.

$^1$H NMR $\delta_{(CD3OD)}$ 1.55-1.71 (2H, m), 2.00-2.27 (7H, m), 2.34 (3H, s), 2.98-3.13 (4H, m), 3.23 (2H, d), 3.26-3.43 (4H, m), 3.52 (1H, d), 3.64 (1H, d), 3.79 (1H, t), 4.61-4.71 (1H, m), 6.96 (1H, d), 7.19-7.26 (1H, m), 7.27-7.35 (5H, m), 7.39-7.46 (3H, m), 7.81-7.86 (2H, m).

EXAMPLE 25

This Example illustrates the preparation of (2S)-2-[4-[[4-(3,4-dichloro-2-methyl-phenoxy)-1-piperidyl]methyl]-1-piperidyl]-3-(4-fluorophenyl)-propanoic acid benzenesulfonic acid salt This compound was prepared following the method of Example 24.

Melting point: 259-260° C.

EXAMPLE 26

This Example illustrates the preparation of (2S)-2-[4-[[4-(3,4-dichloro-2-methyl-phenoxy)-1-piperidyl]methyl]-1-piperidyl]-3-(4-fluorophenyl)-propanoic acid hydrochloride (2S)-2-[4-[[4-(3,4-Dichloro-2-methyl-phenoxy)-1-piperidyl]methyl]-1-piperidyl]-3-(4-fluorophenyl)-propanoic acid (0.75 g) was suspended in ether and a solution of HCl in dioxane (4M, 0.37 mL) was added. The mixture was stirred overnight and then evaporated. The residue was treated with ether and then evaporated and this procedure was repeated several times until a free-flowing solid was obtained. This solid was dried under vacuum at 50° C. overnight. The resultant solid was suspended in methanol with warming and then collected and dried to give the title compound (0.55 g)

Melting point: 281-283° C.

EXAMPLE 26

This illustrates the preparation of 2-Benzyl-2-(4-{[4-(3,4-dichlorophenoxy)piperidin-1-yl]methyl}piperidin-1-yl)butanoic acid This compound was prepared from methyl 2-benzyl-2-(4-{[4-(3,4-dichlorophenoxy)piperidin-1-yl]methyl}piperidin-1-yl)butanoate following the method of Example 4 to give the title compound

MS (APCI$^+$) 519/521 (M+H$^+$)

EXAMPLE 27

This illustrates the preparation of (S)-2-{4-[4-(3,4-dichloro-2-methyl-phenoxy)-piperidin-1-ylmethyl]-piperidin-1-yl}-3-phenyl-propionic acid Tetra-n-butylammonium hydroxide (3.12 g) was dissolved in acetonitrile (5 mL) and added to a suspension of (S)-2-{4-[4-(3,4-dichloro-2-methyl-phenoxy)-piperidin-1-ylmethyl]-piperidin-1-yl}-3-phenyl-propionic acid methyl ester (1.0 g) in acetonitrile (9 mL) at room temperature. The mixture was stirred at this temperature for 3 h then methyl tert-butyl ether (10 mL) was added, followed by water (4 mL). A solution of ammonium acetate (0.89 g) in water (5 mL) was added causing the product to precipitate from solution. The mixture was stirred for 3 h at room temperature and then filtered. The filter cake was washed with water (50 mL) and methyl tert-butyl ether (20 mL). The product was dried under vacuum at 40° C. to give the title compound (0.88 g).

EXAMPLE 28

This illustrates the preparation of (S)-{4-[4-(3,4-dichloro-2-methyl-phenoxy)-piperidin-1-ylmethyl]-piperidin-1-yl}-3-(4-fluoro-phenyl)-propionic acid (Form I)

To (S)-{4-[4-(3,4-dichloro-2-methyl-phenoxy)-piperidin-1-ylmethyl]-piperidin-1-yl}-3-(4-fluoro-phenyl)-propionic acid methyl ester (1 g) in acetonitrile (9 mL) solution (Intermediate 28) was added a solution of tetra-n-butylammonium hydroxide (3.31 g, 48% w/w in water) in acetonitrile (5 mL) over 10 minutes at 20° C.

The reaction mixture was stirred at 20-22° C. for 2 hours. Methyl-tert-butyl ether (10 mL) was added to the reaction mixture followed by a solution of ammonium acetate (0.87 g) in water (5 mL). After 1 h of stirring at room temperature water (5 mL) was added. The precipitate formed was stirred overnight at room temperature.

The solid was filtered and washed (slurry wash) with water (2×4 mL) and methyl tert-butylmethyl ether (6 mL). The solid was dried at 40° C. under reduced pressure overnight to yield the title compound as a colourless solid (0.44 g; melting point 230-237° C., starts degrading at 220° C.).

$^1$H NMR $\delta_{(CD3OD)}$ 1.25-1.40 (2H, m), 1.5-1.65 (1H, m), 1.70-1.90 (4H, m), 1.92-2.10 (2H, m), 2.20-2.25 (2H, m), 2.35 (3H, s), 2.35-2.42 (4H, m) 2.6-2.75 (2H, m), 2.78-2.90 (1H, m), 2.97-3.20 (4H, m), 4.38-4.50 (1H, m), 6.85-7.00 (3H, m), 7.20-7.30 (3H, m)

MS (ES+ve) 523 (M+H)$^+$.

XRPD of Form I is shown in FIG. 1.

| Pos. [°2Th.] | d-spacing [Å] | Rel. Int. [%] |
| --- | --- | --- |
| 2.2272 | 39.63447 | 50.62 |
| 2.6914 | 32.79941 | 35.64 |
| 5.3443 | 16.52252 | 1.17 |
| 7.1482 | 12.35663 | 100 |
| 8.75 | 10.09782 | 3.57 |
| 10.7172 | 8.24831 | 6.89 |
| 12.6424 | 6.9962 | 2.39 |
| 13.2608 | 6.67132 | 10.35 |
| 14.0758 | 6.28685 | 2.26 |
| 14.2953 | 6.19079 | 2.23 |
| 15.1222 | 5.85406 | 1.09 |
| 15.9917 | 5.53767 | 5.72 |
| 17.8742 | 4.95848 | 2.63 |
| 18.2983 | 4.8445 | 7.36 |
| 18.7722 | 4.72326 | 21.26 |
| 19.2498 | 4.60712 | 7.52 |
| 19.7833 | 4.48407 | 4.5 |
| 20.1738 | 4.39815 | 3.34 |
| 21.237 | 4.1803 | 2.3 |
| 22.2454 | 3.99304 | 1.4 |
| 23.3765 | 3.80232 | 2.41 |
| 24.3555 | 3.65165 | 5.04 |
| 24.6251 | 3.61229 | 5.33 |
| 25.4107 | 3.50236 | 2.98 |
| 25.9888 | 3.42575 | 1.53 |
| 26.3646 | 3.37776 | 1.87 |
| 26.8953 | 3.31231 | 1.55 |
| 31.2745 | 2.85777 | 0.79 |
| 33.0542 | 2.70785 | 1.22 |
| 34.2844 | 2.61345 | 1.18 |

EXAMPLE 29

This illustrates the preparation of (S)-{4-[4-(3,4-dichloro-2-methyl-phenoxy)-piperidin-1-ylmethyl]-piperidin-1-yl}-3-(4-fluoro-phenyl)-propionic acid (Form II)

To (S)-{4-[4-(3,4-Dichloro-2-methylphenoxy)-piperidin-1-ylmethyl]-piperidin-1-yl}-3-(4-fluorophenyl)-propionic acid methyl ester (5 g) in acetonitrile (40 mL) was added a solution of tetra-n-butylammonium hydroxide (15.10 g, 48% w/w in water) in acetonitrile (25 mL) over 10 minutes between 10-20° C. The reaction mixture was stirred at 20-22° C. for 2 h. To the reaction mixture was added a solution of ammonium acetate (4.35 g) in water (50 mL) forming a precipitate. A small amount of the solid was withdrawn, isolated by filtration and washed with water three times. The XRPD analysis of this solid indicated that it was form II. The slurry was then stirred overnight at room temperature. A sample of the slurry was again checked by XRPD which showed that it was now form I. The solid was filtered and washed (slurry wash) with water (3×20 mL). The solid was dried in the oven at 40° C. under reduced pressure overnight to yield the title compound as a colourless solid (3.60 g).

XRPD for Form II is shown in FIG. 2

| Pos. [°2Th.] | d-spacing [Å] | Rel. Int. [%] |
| --- | --- | --- |
| 2.2315 | 39.55948 | 99.14 |
| 2.6749 | 33.00216 | 76.85 |
| 5.3589 | 16.47747 | 3.63 |
| 7.186 | 12.29168 | 100 |
| 8.6551 | 10.20831 | 1.83 |
| 10.0439 | 8.79962 | 3.1 |
| 11.0966 | 7.96713 | 1.2 |
| 12.1727 | 7.26509 | 4.68 |
| 13.1501 | 6.72725 | 14.53 |
| 14.3825 | 6.15345 | 3.85 |
| 15.1743 | 5.83409 | 2.28 |
| 17.0236 | 5.20427 | 40.99 |
| 17.3697 | 5.10133 | 64.11 |
| 18.5373 | 4.78257 | 8.87 |
| 19.1233 | 4.63731 | 67.78 |
| 19.3663 | 4.57968 | 30.28 |
| 20.0799 | 4.41851 | 6.99 |
| 21.069 | 4.21325 | 10.79 |
| 22.247 | 3.99275 | 7.08 |
| 22.8768 | 3.88424 | 3.31 |
| 24.417 | 3.64259 | 28.48 |
| 25.1834 | 3.53346 | 18.08 |
| 27.5786 | 3.23177 | 3.67 |
| 33.7683 | 2.6522 | 1.92 |
| 34.6377 | 2.58759 | 6.2 |
| 38.741 | 2.32245 | 1.74 |

EXAMPLE 30

This illustrates the preparation of (2S)-2-(4-{[4-(3,4-dichloro-2-methylphenoxy)piperidin-1-yl]methyl}piperidin-1-yl)-3-(4-fluorophenyl)propanoic acid A Methyl (2S)-2-(4-{[4-(3,4-dichloro-2-methylphenoxy)piperidin-1-yl]methyl}piperidin-1-yl)-3-(4-fluorophenyl)propanoate Powdered sieves (20 g, 4 Å) were added to a solution of methyl (2R)-3-(4-fluorophenyl)-2-hydroxypropanoate (32 g) in dichloromethane (200 mL). The mixture was stirred, under nitrogen, at room temperature, for 15 min then cooled to 0° C. Triflic anhydride (29.9 mL) was added, followed, after 10 min, by 2,6-lutidine (41.4 mL), which was added over approximately 1 h. Stirring was continued for 1 h at 0° C. A solution of 4-(3,4-dichloro-2-methylphenoxy)-1-(piperidin-4-ylmethyl)piperidine (57.6 g) in dichloromethane (600 mL) was added at such a rate that the internal temperature did not exceed 5° C. Triethylamine (49.5 mL) was added dropwise and the mixture was stirred at 0° C. for 1 h. The reaction mixture was filtered through a plug of silica; washing through with dichloromethane. The filtrate was reduced in volume by evaporation under reduced pressure and then washed (×2) with water. The organic fraction was dried (MgSO$_4$), filtered and concentrated in vacuo to give the title compound as a brown oil.

B (2S)-2-(4-{[4-(3,4-dichloro-2-methylphenoxy)piperidin-1-yl]methyl}piperidin-1-yl)-3-(4-fluorophenyl)propanoic acid A solution of lithium hydroxide monohydrate (27.0 g) in water (180 mL) was added dropwise to an ice cooled solution of methyl (2S)-2-(4-{[4-(3,4-dichloro-2-methylphenoxy)piperidin-1-yl]methyl}piperidin-1-yl)-3-(4-fluorophenyl)propanoate (from step A) in methanol (115 mL) and THF (450 mL). The mixture was stirred at room temperature overnight. A solution of ammonium acetate (165 g) in water (300 mL) was added to the reaction mixture, followed by diethyl ether (550 mL). The two phase mixture was stirred rapidly for 5.5 h then solid was collected. The solid was washed with water (2×300 mL) and diethyl ether (3×300 mL) and then dried in a vacuum oven at 40° C. overnight (batch one).

A second batch of solid was collected from the filtrate after standing for 24 h. This was similarly washed with water and diethyl ether then dried (batch two).

Lithium hydroxide monohydrate (1 eq in water) was added to a mixture of batch one in methanol and THF. The free acid was precipitated by addition of ammonium acetate in water. Once again, two crops of crystals were obtained at different time points (batches three and four). Batch three was treated with lithium hydroxide and then ammonium acetate as before to produce two further crops (batches five and six).

The lithium salt of batch two was prepared by addition of lithium hydroxide monohydrate (1 eq in water). This solution was extracted with dichloromethane. A solution of ammonium acetate in water was added to the dichloromethane layer and a solid precipitated which was collected by filtration (batch seven).

Batches four, six and seven were combined and dried to give the title compound (31.19 g).

$^1$H NMR $\delta_{(CD3OD+1\ drop\ NaOD)}$ 1.25 (2H, ddd), 1.50-1.61 (1H, m), 1.72-1.84 (4H, m), 1.94-2.02 (2H, m), 2.22 (2H, d), 2.27-2.40 (7H, m), 2.61-2.68 (2H, m), 2.82 (1H, dd), 2.99-3.08 (3H, m), 3.13 (1H, dd), 4.36-4.43 (1H, m), 6.87-6.95 (3H, m), 7.22-7.27 (3H, m).

MS 521/523 [M−H]$^-$ (APCI−)

EXAMPLE 31

This illustrates the preparation of (2S)-2-(4-{[4-(3,4-dichloro-2-methylphenoxy)piperidin-1-yl]methyl}piperidin-1-yl)-3-phenylpropanoic acid A Methyl (2S)-2-(4-{[4-(3,4-dichloro-2-methylphenoxy)piperidin-1-yl]methyl}piperidin-1-yl)-3-phenylpropanoate Powdered sieves (20 g, 4 Å) were added to a solution of methyl (2R)-2-hydroxy-3-phenylpropanoate (32.8 g) in dichloromethane (200 mL). The mixture was stirred, under nitrogen, at room temperature, for 15 min then cooled to 0° C. Triflic anhydride (33.7 mL) was added, followed, after 10 min, by 2,6-lutidine (46.7 mL), which was added over approximately 1 h. Stirring was continued for 1 h at 0° C. A solution of 4-(3,4-dichloro-2-methylphenoxy)-1-(piperidin- 4-ylmethyl)piperidine (65.0 g) in dichloromethane (600 mL) was added at such a rate that the internal temperature did not exceed 5° C. Triethylamine (55.8 mL) was added dropwise and the mixture was stirred at 0° C. for 1 h. The reaction mixture was filtered though a plug of silica; washing through with dichloromethane. The filtrate was reduced in volume by evaporation under reduced pressure and then washed (×2) with water. The organic fraction was dried (MgSO$_4$), filtered and concentrated in vacuo to give the title compound as a brown oil.

B (2S)-2-(4-{[4-(3,4-Dichloro-2-methylphenoxy) piperidin-1-yl]methyl}piperidin-1-yl)-3-phenylpropanoic acid A solution of lithium hydroxide monohydrate (30.5 g) in water (180 mL) was added dropwise to an ice cooled solution of methyl (2S)-2-(4-{[4-(3,4-dichloro-2-methylphenoxy)piperidin-1-yl]methyl}piperidin-1-yl)-3-phenylpropanoate (from step A) in methanol (115 mL) and THF (450 mL). The mixture was stirred at room temperature overnight. A solution of ammonium acetate (165 g) in water (300 mL) was added to the reaction mixture, followed by tert-butylmethyl ether (300 mL). The two phase mixture was stirred rapidly for 2 h. The solid was collected, washed with water (3×300 mL) and diethyl ether (3×200 mL). The solid was added to diethyl ether and stirred for 1 h then filtered. Fresh diethyl ether was added and the stirring, filtering procedure was repeated. The solid obtained was dried under vacuum at 50° C. overnight to give the title compound (33 g).

$^1$H NMR δ$_{(CD3OD+1\ drop\ NaOD)}$ 1.16-1.35 (2H, m), 1.50-1.62 (1H, m), 1.72-1.84 (4H, m), 1.94-2.03 (2H, m), 2.22 (2H, d), 2.27-2.39 (7H, m), 2.59-2.69 (2H, m), 2.85 (1H, dd), 3.01-3.09 (3H, m), 3.16 (1H, dd), 4.36-4.44 (1H, m), 6.89 (1H, d), 7.11 (1H, dt), 7.17-7.27 (5H, m).

MS 503/505 [M−H]− (APCI−)

EXAMPLE 32

This illustrates the preparation of (2S)-2-(4-{[4-(4-chloro-2-methylphenoxy)piperidin-1-yl]methyl}piperidin-1-yl)-3-(4-fluorophenyl)-2-methylpropanoic acid hydrate (Form A)

Methyl (2S)-2-(4-{[4-(4-chloro-2-methylphenoxy)piperidin-1-yl]methyl}piperidin-1-yl)-3-(4-fluorophenyl)-2-methylpropanoate (34.5 g) and 50% aqueous hydrobromic acid (1.5 l) were heated together at 160° C. for 72 h. The hydrobromic acid was then removed in vacuo. The resulting solid was dissolved in a 3:1 mixture of acetonitrile:water (350 ml) and a solution of lithium hydroxide monohydrate (7 g) in water (50 ml) was added. A solution of ammonium acetate (15.42 g) in water (30 ml) was then added, followed by isohexane (150 ml). The mixture was then stirred vigorously for 1 h. and allowed to stand for 1 h. The solid precipitate was collected, washed well with diethyl ether and dried overnight in vacuo. The solid was recrystallised from 3:1 acetonitrile:water (400 ml) to give the title compound (21 g) as a channel hydrate (Form A).

3.85% water (Karl-Fischer analysis)

MS ES+ (+ve) 503/505 (M+H)+

$^1$H NMR δ$_{(CD3OD)}$ 1.32 (3H, s), 1.41-1.68 (2H, m), 1.72-1.84 (3H, m), 1.85-2.13 (4H, m), 2.15 (3H, s), 2.24-2.29 (2H, m), 2.31-2.41 (2H, m), 2.61-2.76 (2H, m), 2.96-3.09 (3H, m), 3.18 (1H, d), 3.32-3.40 (1H, m), 3.59-3.72 (1H, m), 4.30-4.42 (1H, m), 6.85 (1H, d), 6.96 (2H, t), 7.03-7.11 (2H, m), 7.23-7.31 (2H, m)

Figure 3:
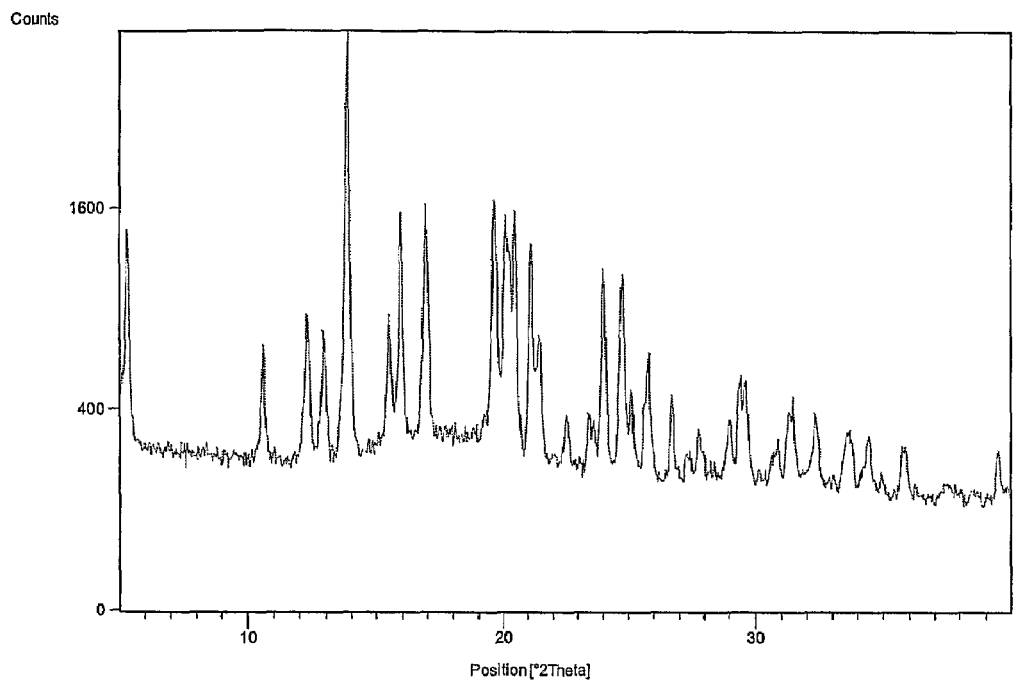

XRPD for Form A is shown in FIG. 3

| Pos. [°2Th.] | d-spacing [Å] | Rel. Int. [%] |
|---|---|---|
| 5.3042 | 16.64746 | 38.18 |
| 10.6081 | 8.33289 | 15.1 |
| 12.2996 | 7.19041 | 21.34 |
| 12.9368 | 6.83768 | 17.84 |
| 13.8637 | 6.38254 | 100 |
| 15.4899 | 5.71594 | 21.07 |
| 15.9475 | 5.55295 | 43.36 |
| 16.9292 | 5.23307 | 45.21 |
| 19.6122 | 4.52282 | 46.88 |
| 20.0506 | 4.4249 | 39.58 |
| 20.4452 | 4.34037 | 43.68 |
| 21.1148 | 4.20421 | 37.21 |
| 21.4664 | 4.13615 | 17.97 |
| 22.5577 | 3.93845 | 5.89 |
| 23.5073 | 3.78147 | 5.72 |
| 24.0362 | 3.69943 | 31.3 |
| 24.7697 | 3.59152 | 30.35 |
| 25.1369 | 3.53988 | 10.04 |
| 25.8045 | 3.4498 | 15.74 |
| 26.74 | 3.33119 | 9.4 |
| 27.8356 | 3.20251 | 4.01 |
| 29.399 | 3.03566 | 11.28 |
| 29.642 | 3.01133 | 11.65 |
| 31.3761 | 2.84874 | 7.22 |
| 32.3322 | 2.76665 | 7.42 |
| 33.6764 | 2.65923 | 5.23 |
| 34.41 | 2.6042 | 4.99 |
| 35.8167 | 2.50508 | 4.12 |

EXAMPLE 33

This illustrates the preparation of (2R)-2-(4-{[4-(4-Chloro-2-methylphenoxy)piperidin-1-yl]methyl}piperidin-1-yl)-3-(4-fluorophenyl)-2-methylpropanoic acid This was prepared following the method of Example 32 using methyl (2R)-2-(4-{[4-(4-chloro-2-methylphenoxy)piperidin-1-yl]methyl}piperidin-1-yl)-3-(4-fluorophenyl)-2-methylpropanoate.

$^1$H NMR δ$_{(CD3OD)}$ 1.31 (3H, s), 1.50 (1H, q), 1.62 (1H, q), 1.73-1.84 (2H, m), 1.85-2.12 (5H, m), 2.16 (3H, s), 2.31 (2H, d), 2.35-2.46 (2H, m), 2.66-2.78 (2H, m), 2.95-3.11 (3H, m), 3.18 (1H, d), 3.36 (1H, d), 3.60-3.71 (1H, m), 4.33-4.43 (1H, m), 6.86 (1H, d), 6.96 (2H, t), 7.03-7.11 (2H, m), 7.26 (2H, t)

MS (ES−ve) 501/503 (M−H)+

EXAMPLES 34

(2S)-2-(4-{[4-(4-Chloro-2-methylphenoxy)piperidin-1-yl]methyl}piperidin-1-yl)-3-(4-fluorophenyl)-2-methylpropanoic acid Form B (2S)-2-(4-{[4-(4-Chloro-2-methylphenoxy)piperidin-1-yl]methyl}piperidin-1-yl)-3-(4-fluorophenyl)-2-methylpropanoic acid (for example amorphous or crystalline) can initially be partly dissolved in an organic solvent and stirred until Form B is obtained. The process involves a solution mediated transformation in the slurry without complete dissolution of the starting material. This transformation is thermodynamically driven to yield a more stable form with a lower solubility under the conditions evaluated.

Form B is typically formed when a slurry of Form A of (2S)-2-(4-{[4-(4-chloro-2-methylphenoxy)piperidin-1-yl]methyl}piperidin-1-yl)-3-(4-fluorophenyl)-2-methylpropanoic acid is stirred in ethanol at 25° C. or 60° C. for greater than 1 day.

XRPD for (2S)-2-(4-{[4-(4-Chloro-2-methylphenoxy)piperidin-1-yl]methyl}piperidin-1-yl)-3-(4-fluorophenyl)-2-methylpropanoic acid ethanol solvate Form B is shown in FIG. 4

| Pos. [°2Th.] | d-spacing [Å] | Rel. Int. [%] |
|---|---|---|
| 7.6772 | 11.50625 | 32.02 |
| 8.9078 | 9.91929 | 3.67 |
| 13.307 | 6.64824 | 100 |
| 13.7582 | 6.43123 | 6.47 |
| 15.2087 | 5.82096 | 32.61 |
| 15.4305 | 5.73779 | 15.65 |
| 16.3607 | 5.41362 | 6.19 |
| 17.3791 | 5.09859 | 18.01 |
| 18.3842 | 4.82206 | 71.89 |
| 19.6742 | 4.5087 | 87.16 |
| 20.0571 | 4.42348 | 6.95 |
| 20.6439 | 4.29904 | 13.54 |
| 21.6962 | 4.09284 | 43.29 |
| 22.7189 | 3.91087 | 19.79 |
| 23.0611 | 3.85361 | 8.87 |
| 24.3742 | 3.6489 | 5.79 |
| 26.3108 | 3.38455 | 2.6 |
| 26.7429 | 3.33083 | 4.82 |
| 29.037 | 3.07268 | 1.93 |
| 29.8487 | 2.99095 | 1.32 |
| 32.0179 | 2.79309 | 2.41 |

EXAMPLE 35

Histamine H1 receptor binding activity of compounds of the invention was assessed by competition displacement of 1 nM [3H]-pyrilamine (Amersham, Bucks, Product code TRK 608, specific activity 30 Ci/mmol) to 2 µg membranes prepared from recombinant CHO-K1 cells expressing the human H1 receptor (Euroscreen SA, Brussels, Belgium, product code ES-390-M) in assay buffer (50 mM Tris pH 7.4 containing 2 mM $MgCl_2$, 250 mM sucrose and 100 mM NaCl) for 1 hour at room temperature.

The following compounds of the invention gave inhibition of [3H]pyrilimine binding:

| Example | H1 pKi |
|---|---|
| 3 | 7.5 |
| 4 | 7.1 |
| 6 | 7.5 |
| 13 | 7.0 |

EXAMPLE 36

Eotaxin-2-Induced Shape Change in Eosinophils in Human Blood In Vitro

See for example, Differential regulation of eosinophil chemokine signaling via CCR3 and non-CCR3 pathways. Sabroe I, Hartnell A, Jopling L A, Bel S, Ponath P D, Pease J E, Collins P D, Williams T J. J. Immunol. 1999 Mar. 1; 162(5):2946-55.

Human blood, collected by venous puncture into 9 mL lithium-heparin tubes, was incubated with the CCR3 agonist eotaxin-2 in the presence of vehicle (0.1% (v/v) DMSO) or test compound for 4 min at 37° C. in a deep, 96-square-well plate. The blood was fixed with Optilyse B (100 µL) at room temperature for 10 min and then the red blood cells were lysed with distilled water (1 mL) for 60 min at room temperature.

The plate was centrifuged at room temperature for 5 min at 300 g. The pellet was re-suspended in assay buffer (PBS without $CaCl_2$ and $MgCl_2$, containing HEPES (10 mM), Glucose (10 mM) and 0.1% (w/v) BSA, pH 7.4)) and the samples were analysed using flow cytometry (FC500, Beckman Coulter). The high autofluorescence of eosinophils allowed them to be identified as a discrete population from the other blood cell types. Eosinophil shape was monitored as the refractive index of the eosinophil population as determined using the forward scatter signal in flow cytometry.

Eotaxin-2 induced a concentration-dependent change in the forward scatter of eosinophils and these data were used to construct a concentration effect curve (E/[A] curve). The rightward displacement of the eotaxin-2 E/[A] curve in the presence of a CCR3 antagonist was used to estimate a $pA_2$ value in blood using the following equation:

$$\text{Single } pA_2 = -\log_{10}([B]/(r-1))$$

where r is the ratio of the concentrations required for half maximal effects of eotaxin-2 in the absence and presence of antagonist ($[A]_{50}$ for eotaxin-2 in the presence of antagonist divided by $[A]_{50}$ for control eotaxin-2 curve) and [B] is the molar concentration of antagonist.

The following compounds of the invention gave inhibition of shape-change:

| Example | CCR3 $pA_2$ |
|---|---|
| 1 | 7.3 |
| 2 | 7.7 |
| 3 | 7.7 |
| 4 | 7.6 |
| 5 | 7.9 |
| 6 | 8.2 |
| 12 | 8.0 |
| 13 | 6.7 |
| 14 | 6.7 |
| 16 | 7.1 |
| 20 | 7.2 |
| 21 | 7.3 |
| 22 | 7.3 |
| 23 | 7.2 |
| 24 | 7.2 |
| 25 | 7.3 |
| 26 | 7.3 |

EXAMPLE 37

Determination of Compound Affinity at Human Recombinant CCR3 Receptors Assessed by Competition of [$^3$H]-4-(2,4-dichloro-3-methylphenoxy)-1'-[4-(methylsulfonyl)benzoyl]-1,4'-bipiperidine for CHO-K1 Cell Membranes In Vitro Membranes, prepared from CHO-K1 cells stably expressing recombinant human CCR3, suspended in assay buffer (50 mM Tris-Base, pH 7.4; containing sodium chloride (100 mM) and magnesium chloride (2 mM)) were incubated in the presence of 2 nM [$^3$H]-4-(2,4-dichloro-3-methylphenoxy)-1'-[4-(methylsulfonyl)benzoyl]-1,4'-bipiperidine, along with vehicle (1% (v/v) DMSO), 4-(4-chloro-3-methylphenoxy)-1'-[2-(methylsulfonyl)benzoyl]-1,4'-bipiperidine (to define non-specific binding) or test compound for 2 h at 37° C. in round bottomed 96-well plates. The plates were then filtered onto GF/B filter plates, pre-soaked for 1 hour in plate-coating solution (0.3% (w/v) polyethylenimine, 0.2% (w/v) BSA in de-ionised water), using a 96-well plate Tomtec cell harvester. Four washes (250 µL) with wash buffer (50 mM Tris-Base, pH 7.4 containing sodium chloride (500 mM) and magnesium chloride (2 mM)) were performed at 4° C. to remove unbound radioactivity. Plates were dried and MicroScint-O (50 µL) was added to each well. The plates were sealed (TopSeal A) and filter-bound radioactivity was measured with a scintillation counter (TopCount, Packard BioScience) using a 1 minute counting protocol.

Specific binding was determined from values of the control wells minus the values for the NSB wells for each assay plate. $pIC_{50}$ values were calculated using a four parameter logistic fit (where $pIC_{50}$ is defined as the negative logarithm of the concentration of compound required for 50% reduction in specific [$^3$H]-4-(2,4-dichloro-3-methylphenoxy)-1'-[4-(methylsulfonyl)benzoyl]-1,4'-bipiperidine binding). Data were presented as mean pKi values (calculated by applying a Cheng-Prussof correction to $pIC_{50}$ values) from a minimum of 2 separate experiments.

The following compounds of the invention gave inhibition of binding:

| Example | CCR3 pKi |
| --- | --- |
| 1 | 9.3 |
| 2 | 9.2 |
| 3 | 9.3 |
| 4 | 9.1 |
| 5 | 9.2 |
| 6 | 9.7 |
| 8 | 7.6 |
| 9 | 8.6 |
| 10 | 8.3 |
| 11 | 8.8 |
| 12 | 9.7 |
| 13 | 8.9 |
| 14 | 9.3 |
| 15 | 8.2 |
| 16 | 8.9 |
| 17 | 9.3 |
| 18 | 8.4 |
| 19 | 8.3 |
| 20 | 8.7 |
| 21 | 9.3 |
| 22 | 9.3 |
| 23 | 8.7 |
| 24 | 8.7 |
| 25 | 9.3 |
| 26 | 9.3 |

The invention claimed is:

1. The compound (2S)-2-(4-{[4-(4-chloro-2-methylphenoxy)piperidin-1-yl]methyl}piperidin-1-yl)-3-(4-fluorophenyl)-2-methylpropanoic acid, or a pharmaceutically acceptable salt thereof.

2. A pharmaceutically acceptable salt of (2S)-2-(4-{[4-(4-chloro-2-methylphenoxy)piperidin-1-yl]methyl}piperidin-1-yl)-3-(4-fluorophenyl)-2-methylpropanoic acid which is a sodium, potassium or $(CH_2CH_2OH)_3NH^+$ salt, or a hydrochloride, dihydrochloride, hydrobromide, phosphate, sulfate, acetate, fumarate, maleate, malonate, succinate, tartrate, citrate, oxalate, methanesulfonate, benzenesulfonate or p-toluenesulfonic acid salt.)

3. The compound (2S)-2-(4-{[4-(4-chloro-2-methylphenoxy)piperidin-1-yl]methyl}piperidin-1-yl)-3-(4-fluorophenyl)-2-methylpropanoic acid.

* * * * *